US009255956B2

(12) United States Patent
Sebesta et al.

(10) Patent No.: US 9,255,956 B2
(45) Date of Patent: Feb. 9, 2016

(54) APPARATUS THAT CAN BE ELECTRICALLY OPERATED VIA A MAINS VOLTAGE CONNECTION

(75) Inventors: Sven Sebesta, Schweinfurt (DE); Ulrich Wernicke, Mittelherwigsdorf (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 341 days.

(21) Appl. No.: 13/820,605

(22) PCT Filed: Sep. 2, 2011

(86) PCT No.: PCT/EP2011/004438
§ 371 (c)(1),
(2), (4) Date: Mar. 4, 2013

(87) PCT Pub. No.: WO2012/028329
PCT Pub. Date: Mar. 8, 2012

(65) Prior Publication Data
US 2013/0165848 A1    Jun. 27, 2013

(30) Foreign Application Priority Data
Sep. 3, 2010   (DE) .......................... 10 2010 036 295

(51) Int. Cl.
*A61M 1/16*   (2006.01)
*A61M 1/28*   (2006.01)
*A61M 5/44*   (2006.01)
(Continued)

(52) U.S. Cl.
CPC .............. *G01R 31/021* (2013.01); *A61M 1/166* (2014.02); *A61M 1/28* (2013.01); *A61M 5/445* (2013.01);
(Continued)

(58) Field of Classification Search
CPC ....... B01D 61/30; B01D 61/32; A61M 1/166; A61M 1/1664; A61M 5/44; A61M 5/445; A61M 2205/127; A61M 2205/36; A61M 2205/3633; A61M 2205/3653; A61M 1/16; A61M 1/28; G01R 35/00; G01R 31/12; G01R 31/121; G01R 31/1227; H05B 31/26; H05B 2203/017; H05B 2203/021; H05B 3/26
USPC ........ 210/85, 175, 184, 321.6, 646; 604/5.01, 604/6.09, 29; 324/551; 340/657, 660, 661, 340/664; 174/70, 70 R; 219/542, 548
See application file for complete search history.

(56) References Cited

U.S. PATENT DOCUMENTS 4,025,139 A * 5/1977 Martucci ........................ 439/106
4,155,852 A * 5/1979 Fischel et al. ................. 210/186
(Continued)

FOREIGN PATENT DOCUMENTS

| DE | 41 08 804 | 9/1992 |
|----|-----------|--------|
| DE | 44 42 825 | 6/1995 |
| EP | 1 263 549 | 12/2002 |
| EP | 1 623 733 | 2/2006 |
| EP | 1 222 087 | 3/2006 |
| WO | WO 03/099355 | 12/2003 |
| WO | WO 2009/044220 | 4/2009 |

(Continued)

*Primary Examiner* — Joseph Drodge
(74) *Attorney, Agent, or Firm* — Jacobson Holman, PLLC.

(57) ABSTRACT

The present invention relates to a device operable electrically via a mains voltage connection, in particular without a ground wire connection, having a live element and having an application part, wherein the application part is insulated by a basic insulation with respect to the live element. In this respect, an insulation monitor is provided which monitors the quality of the basic insulation of the application part with respect to the live element. The present invention furthermore comprises a medical device having a heating module for heating a medical fluid, wherein the heating module comprises a heating element having a heating coil arranged on a first ceramic layer, wherein the heating element is arranged on a second ceramic layer, wherein the second ceramic layer advantageously forms a heating plate of the heating module.

17 Claims, 17 Drawing Sheets

Figure 1A:
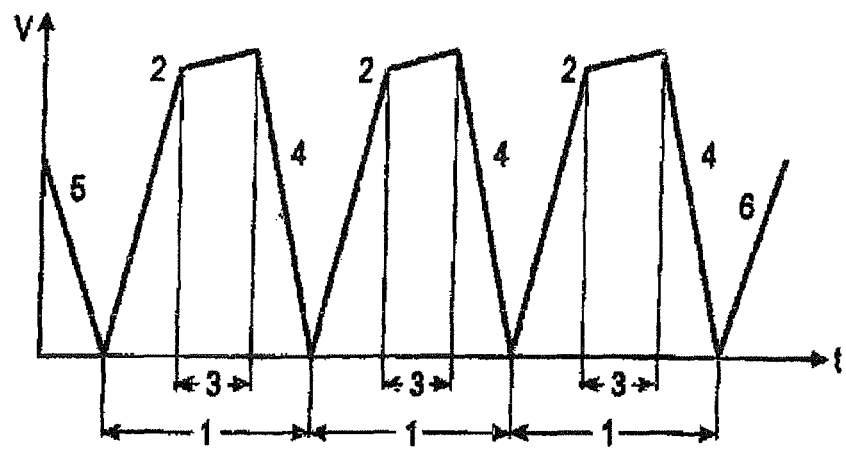

(51) Int. Cl.
*B01D 61/30* (2006.01)
*B01D 61/32* (2006.01)
*G01R 31/02* (2006.01)
*G01R 31/12* (2006.01)
*H05B 3/26* (2006.01)
*G01R 35/00* (2006.01)

(52) U.S. Cl.
CPC ............... *B01D 61/30* (2013.01); *B01D 61/32* (2013.01); *G01R 31/12* (2013.01); *H05B 3/26* (2013.01); *A61M 1/16* (2013.01); *A61M 2205/122* (2013.01); *A61M 2205/127* (2013.01); *A61M 2205/3653* (2013.01); *G01R 35/00* (2013.01); *H05B 2203/017* (2013.01); *H05B 2203/021* (2013.01)

(56) References Cited

U.S. PATENT DOCUMENTS

| | | | | |
|---|---|---|---|---|
| 5,287,062 | A * | 2/1994 | Pellegrin et al. | 324/551 |
| 5,712,572 | A * | 1/1998 | Tamechika et al. | 324/551 |
| 5,736,038 | A * | 4/1998 | Stoughton | 210/243 |
| 5,760,488 | A | 6/1998 | Sonntag | |
| 6,489,782 | B1 * | 12/2002 | Baier et al. | 324/551 |
| 2002/0079906 | A1 * | 6/2002 | Rashkes et al. | 324/544 |
| 2003/0104764 | A1 | 6/2003 | Preising | |
| 2003/0217962 | A1 | 11/2003 | Childers et al. | |
| 2006/0055246 | A1 | 3/2006 | Jansen et al. | |
| 2007/0012349 | A1 * | 1/2007 | Gaudiana et al. | 136/244 |
| 2010/0312161 | A1 * | 12/2010 | Jonsson et al. | 604/5.01 |

* cited by examiner

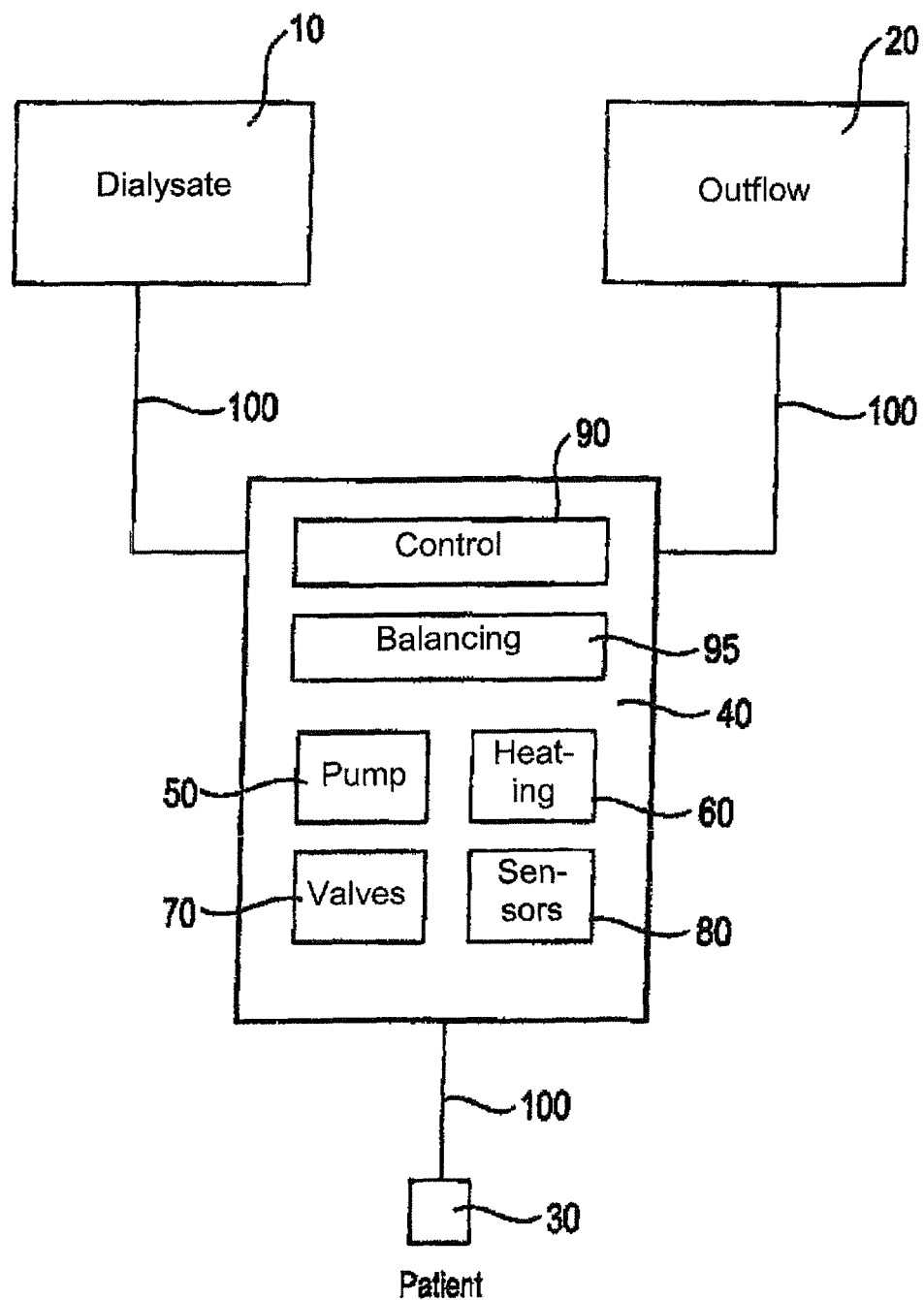

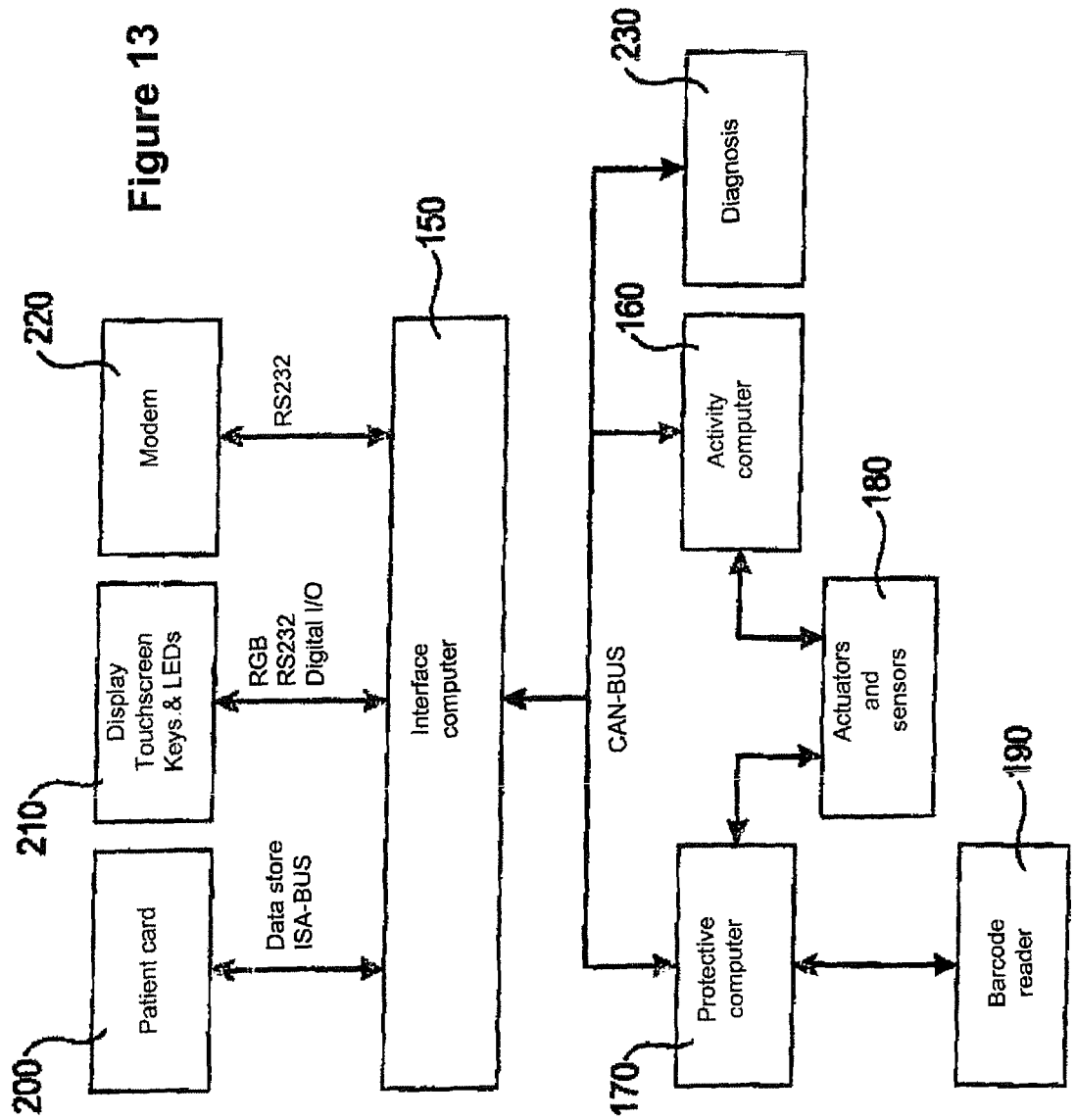

APPARATUS THAT CAN BE ELECTRICALLY OPERATED VIA A MAINS VOLTAGE CONNECTION

This is a national stage of PCT/EP11/004438 filed Sep. 2, 2011 and published in German, which has a priority of Germany no. 10 2010 036 295.6 filed Sep. 3, 2010, hereby incorporated by reference.

The present invention relates to a device operable electrically via a mains voltage connection having a live element and having an application part, wherein the application part is insulated by a basic insulation with respect to the live element. It is in particular a device without a ground wire connection. The present invention further relates to a medical device, in particular to a dialysis machine having a heating module for heating a medical fluid, wherein the heating module comprises a heating element having a heating coil arranged on a first ceramic layer.

If devices are operated at mains voltage, it must be prevented that users of the device are endangered by an electric shock. It must in particular be prevented in this respect that a dangerous electrical current flows through the human body when a user comes into contact with the application part. For this purpose, a basic insulation is first provided between the live elements of the device and the application part which serves as a basic protection in accordance with the classification of the protective measures.

However, a fault protection is furthermore required in addition to such a basic protection. Such a fault protection should prevent any danger arising for the user on a failure of the basic protection, that is, on a defective insulation between the live element and the application element. In this respect, the use of a ground wire, that is, the grounding of the device, or the use of an isolating transformer for the galvanic decoupling of the live parts from the mains voltage are known for fault protection. A ground wire connection is, however, not available everywhere and an isolating transformer results in an increase in construction space, weight and costs.

This problem is particularly relevant in devices having a large ohmic consumer such as a heating module. Such heating modules are in this respect in particular used in medical devices, such as in a dialysis machine, to heat a medical fluid. Such heating modules usually have a heating element with a heating coil arranged on a first ceramic layer, with the heating coil being supplied with power via the mains voltage.

It is therefore the object of the present invention to provide a device operable at a mains voltage connection which has a further fault protection by a basic insulation in addition to the basic protection. It is a further object of the present invention to provide a medical device having an improved heating module.

These objects are achieved in accordance with the invention by devices in accordance with claims 1 and 10. Advantageous embodiments of the present invention form the subject of the dependent claims.

The present invention relates in a first aspect to a device operable electrically via a mains voltage connection having a live element and having an application part, wherein the application part is insulated by a basic insulation with respect to the live element. In accordance with the invention, an insulation monitor is provided which monitors the quality of the basic insulation of the application part with respect to the live element. The insulation monitor in particular in this respect monitors the performance, i.e. the transfer resistance, of the basic insulation. It is possible by the insulation monitor constantly to monitor the quality of the basic insulation with respect to the user part and thus to protect the user from a dangerous electric shock if the basic insulation were to fail. The monitoring by the insulation monitor can thus be seen as a second protective measure and allows the device to be operated without a ground wire. The present invention is therefore in particular used in those devices which do not have a ground wire. The fault protection otherwise provided by the ground wire is thus provided by the insulation monitor.

Insulation monitors have previously only been used in the art in so-called IT systems in which a definable region of a power supply system is isolated from the remaining power supply system by an isolating transformer, with a grounding of the isolated region of the power supply system being dispensed with. The insulation monitors used in such IT systems in this respect monitor the quality of the insulation of the mains with respect to a ground connection. If this quality degrades, warnings are usually output. Since the isolated region of the power supply system is, however, not grounded, no acute danger emanates from only one fault in the insulation so that a disconnection of the mains is not necessary. In contrast, other usage possibilities for insulation monitors were previously unknown in the prior art.

Unlike in the prior art, it is not the insulation between a power supply system and a ground connection which is monitored by the insulation monitor in accordance with the invention, but rather the quality of the basic insulation of an application part of the device with respect to a live element of the device. In addition, the device in accordance with the invention can also be operated at a mains voltage connection which is grounded.

In accordance with the invention, the device is advantageously a medical device. In this respect, the insulation monitor makes it possible to operate this medical device without a ground wire so that it becomes usable in a more versatile manner. It is in particular a question of a dialysis machine in accordance with the invention.

Provision is furthermore made in accordance with the invention that the insulation monitor determines a current flow and/or resistance between the live element and the application part. In this respect, the insulation monitor can be based both on a passive measurement principle and on an active measurement principle. With a passive measurement principle, the insulation monitor only passively determines a current flow between the live element and the application part. The quality of the basic insulation can be determined from the magnitude of this current flow. With an active measurement method, the insulation monitor, in contrast, applies a voltage signal between the live element and the application part and determines the current flow resulting therefrom. The resistance of the basic insulation and thus its quality can be determined from this. The insulation monitor is for this purpose in particular electrically conductively connected to the live element and to the application part via connection lines. In this respect, in accordance with the invention, the current flow and/or resistance between the application part and at least one voltage feed of the live element can be determined.

Provision is further advantageously made that the insulation monitor respectively determines the current flow and/or resistance between the application part and a first voltage feed of the live element and the current flow and/or resistance between the application part and a second voltage feed of the live element. The quality of the basic insulation can be reliably determined by the measurement of the current flow and/or of the resistance between the application part and the two voltage feeds.

The present invention is advantageously used in those devices in which the live element is operated without a galvanic isolation at the mains voltage. Such a galvanic isolation, e.g. by an isolation transformer, can in particular be dispensed with by the insulation monitor without endangering the safety of a user.

The insulation monitor advantageously switches the power supply of the live element off in accordance with the invention when it recognizes a defective basic insulation. If therefore the current flow between the live element and the application part exceeds a specific limit value and if the resistance between the live element and the application part is below a specific limit value, the insulation monitor concludes from this that the basic insulation is defective and switches off the power supply of the live element to protect the user from a dangerous electric current flow through his body on contact with the application part. In this respect, both voltage feeds of the live element are advantageously interrupted.

Alternatively or additionally to the switching off of the power supply for the live element, the insulation monitor can advantageously advice the device controller that the basic insulation is defective. In this respect, a display can in particular take place which draws the operator's attention to the defectiveness of the basic insulation. Alternatively, the power supply of the total device can be switched off.

Further advantageously, the device controller of the device has a function for testing the proper function of the insulation monitor. In this respect, an initializing test can in particular be carried out when the device is put into operation which ensures the proper function of the insulation monitor. For this purpose, the basic insulation can be bridged via a switch and a resistor and a check can be made in so doing whether the insulation monitor recognizes this.

The present invention can in particular be used in a device in which the live element represents a consumer with a relatively high power consumption. In such consumers, an isolating transformer would require a correspondingly large dimensioning which can now be dispensed with. The live element in this respect in particular has a consumption of more than 100 W, further advantageously of more than 500 W.

The live element in accordance with the present invention can in particular be a heating element. It can in particular be a ceramic heating element. With such a heating element, a resistance path is arranged on a ceramic board. The resistance path is heated by the application of a voltage to it and it outputs the heat to the ceramic board. The ceramic board in this respect simultaneously serves as the basic insulation. The present invention can, however, also be used with other live elements, e.g. with motors or similar.

The application part of the device in accordance with the invention is in particular an element of the device which a user could touch on the operation of the device. It is furthermore in particular an electrically conductive element or an element made of metal.

The application part can furthermore be a housing element. The application part is in this respect in particular a heating plate which is heated via a heating element and is isolated from it by the basic insulation. Such a heating plate can in particular be a metal plate, in particular an aluminum plate.

The present invention is in particular in this respect used in a dialysis machine, wherein the live element represents a ceramic heating element and the application part represents a heating plate, with both being insulated from one another by the ceramic layer of the ceramic heating element. The dialyzate can advantageously be heated via this heating element. A heating region of the fluid system can in this respect in particular be coupled to the heating plate. The insulation monitor in accordance with the invention in this respect allows the operation of such a dialysis machine without a ground wire connection.

The present invention furthermore includes a method for operating an electrical device via a mains voltage connection, wherein the device has a live element and an application part and wherein the application part is isolated from the live element by a basic insulation. Provision is made in accordance with the invention that the quality of the basic insulation of the application part is monitored with respect to the live element. In this respect, in particular the quality of the basic insulation is constantly monitored and the switching off of the power supply of the live element is carried out on an exceeding of a limit value.

The method in accordance with the invention is advantageously carried out as has already been described above with respect to the device in accordance with the invention. The method in accordance with the invention is in particular a method for operating an electrical device such as has been described above.

In a second aspect, the present invention includes a medical device with a heating module for heating a medical fluid, wherein the heating module includes a heating element with a heating coil arranged on a first ceramic layer. Provision is made in this respect in accordance with the invention that the heating element is arranged on a second ceramic layer. Due to the second ceramic layer on which the heating element is arranged in accordance with the invention, a second insulation is thus provided by the construction design of the heating module which provides an improved protection of the user in addition to the base insulation formed by the first ceramic layer.

The medical device can in particular be a dialysis machine, wherein the heating module is used for heating dialysate and/or blood. It can in particular be a peritoneal dialysis machine in which the heating module is used for heating the dialysate.

The second ceramic layer which is provided in accordance with the second aspect of the present invention can advantageously form the heating plate of the heating module. The fluid paths of the medical device can advantageously be coupled to this heating plate in order to heat the medical fluid located in the fluid paths.

The heating coil is in this respect advantageously a resistance path which is applied to the first ceramic layer. Connectors are in this respect advantageously provided to connect the heating coil to the supply voltage.

The medical device in accordance with the invention is advantageously operated via a mains voltage connector. It can in particular be a device without a ground wire connection in this respect. In this respect, the heating can nevertheless be operated without an isolating transformer due to the further insulation provided by the second ceramic layer.

In a preferred embodiment of the present invention, the first and/or the second ceramic layer comprise(s) aluminum oxide or aluminum nitride. Both materials have very good heat-conducting properties and are simultaneously excellent electrical insulators. In a particularly preferred embodiment, in this respect the first ceramic layer comprises aluminum oxide, while the second ceramic layer comprises aluminum nitride.

The heating element with the first ceramic layer is preferably adhered to the second ceramic layer. The adhesion in particular takes place in this respect areally over the total surface of the heating element. Different coefficients of expansion of the materials used for the two layers can be compensated by the use of an adhesive for connecting the ceramic layer of the heating element to the second ceramic layer.

The adhesive is in this respect advantageously a thermally conductive adhesive, in particular a silicone adhesive.

In a preferred embodiment, a plate forms both the first ceramic layer and the second ceramic layer. In this respect, the plate forming the second ceramic layer is advantageously larger than the plate forming the first ceramic layer. The plate forming the second ceramic layer can thus form a support element for the heating element with the first ceramic layer.

The plate forming the second ceramic layer advantageously does not have any apertures in the region in which the heating coil is arranged on the first ceramic layer. The second ceramic layer advantageously does not have any apertures at all in the regions in which the first ceramic layer is provided. Further advantageously, the plate forming the second ceramic layer has no apertures at all.

Further advantageously, the first ceramic layer also has no apertures in the region of the heating coil and particularly advantageously no apertures at all.

The insulation safety is increased by the design of the ceramic layers as free of apertures as possible.

Furthermore, one or more temperature sensors can be provided on the heating element of the heating module. A temperature sensor can in this respect in particular be arranged on the same side of the first ceramic layer on which the heating coil is also arranged.

The first ceramic layer can preferably have a thickness between 0.5 mm and 2 mm, further preferably a thickness between 0.8 and 1.2 mm.

The second ceramic layer advantageously has a thickness between 1 mm and 3 mm, further advantageously between 1.2 mm and 1.8 mm.

The layer thickness of the adhesive layer which connects the two ceramic layers to one another can amount to between 0.01 mm and 1 mm, advantageously between 0.1 mm and 0.5 mm.

The heating elements used in the present invention can in this respect advantageously have a maximum power between 100 W and 2000 W, further advantageously between 200 and 1000 W.

In a particular embodiment of the present invention, at least two heating elements are provided which are arranged on a common second ceramic layer. The second ceramic layer in this respect advantageously in turn forms a heating plate on which two heating elements with their respective first ceramic layers are thus arranged next to one another. The structure of the heating module and of the heating elements advantageously otherwise corresponds to the design as was represented above.

The two heating elements are in this respect advantageously electrically connected to one another at the rear via a line with integrated thermal fuse. The two heating elements can in particular be connected in series in this respect.

In a further advantageous embodiment of the present invention, the heating modules furthermore has a frame. In this respect, the second ceramic layer can in particular be adhered to such a frame to increase the stability of the heating module.

Provision can furthermore be made that the heating module is vulcanized in the medical device. A particularly good seal hereby results.

The present invention furthermore includes a heating module for a medical device such as was described above. The heating module in particular includes in this respect a heating element with a heating coil arranged on a first ceramic layer, with the heating element being arranged on a second ceramic layer. The second ceramic layer is in this respect in particular the heating plate of the heating module. The heating module is in this respect advantageously designed as was already shown in more detail above with respect to the medical device.

The second aspect of the present invention, in which a second ceramic layer is used for improved insulation, can in this respect also be combined in accordance with the invention with the first aspect of the present invention in which an insulation monitor is provided. A further higher security hereby results.

The present invention will now be presented in more detail with reference to embodiments and to drawings.

The device in accordance with the invention electrically operable via a mains voltage connection and the medical device in accordance with the invention is a dialysis machine in an advantageous embodiment. The design of such a dialysis machine in which the present invention is used will therefore first be generally presented in more detail with reference of FIGS. 1 to 13. Embodiments of the first aspect of the present invention will then be presented in more detail with reference to FIGS. 14 to 16, an embodiment of the second aspect of the present invention will be presented in more detail with reference to FIG. 17.

Figure 1B:
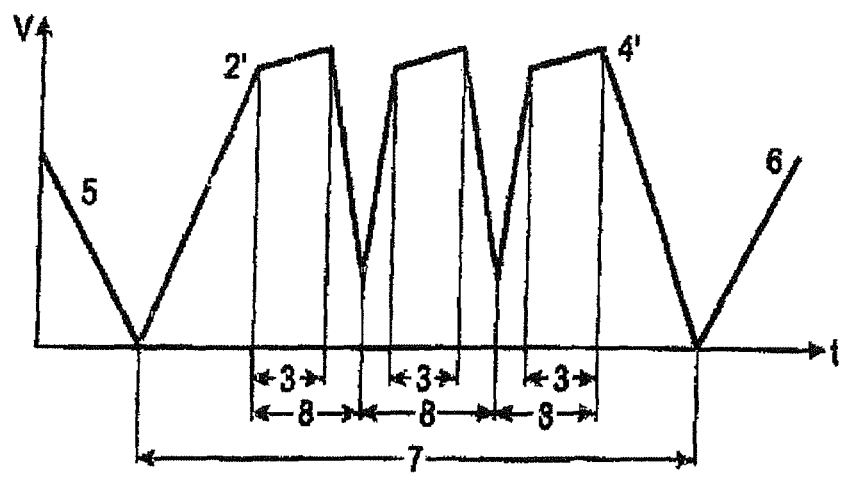
Figure 1C:
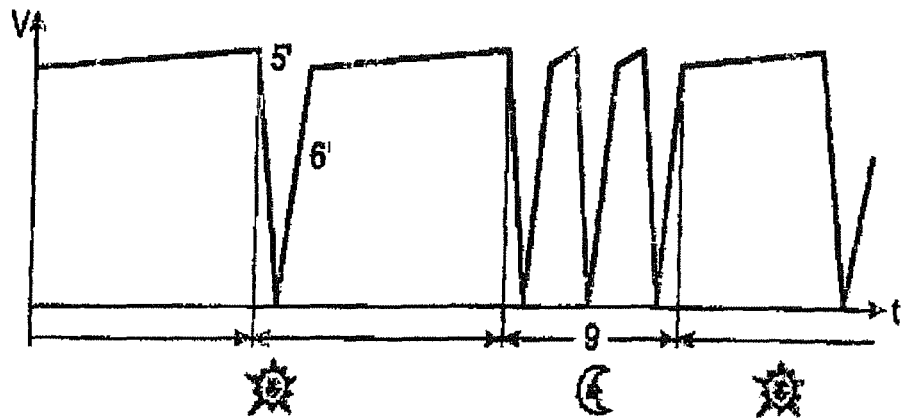
Figure 3:
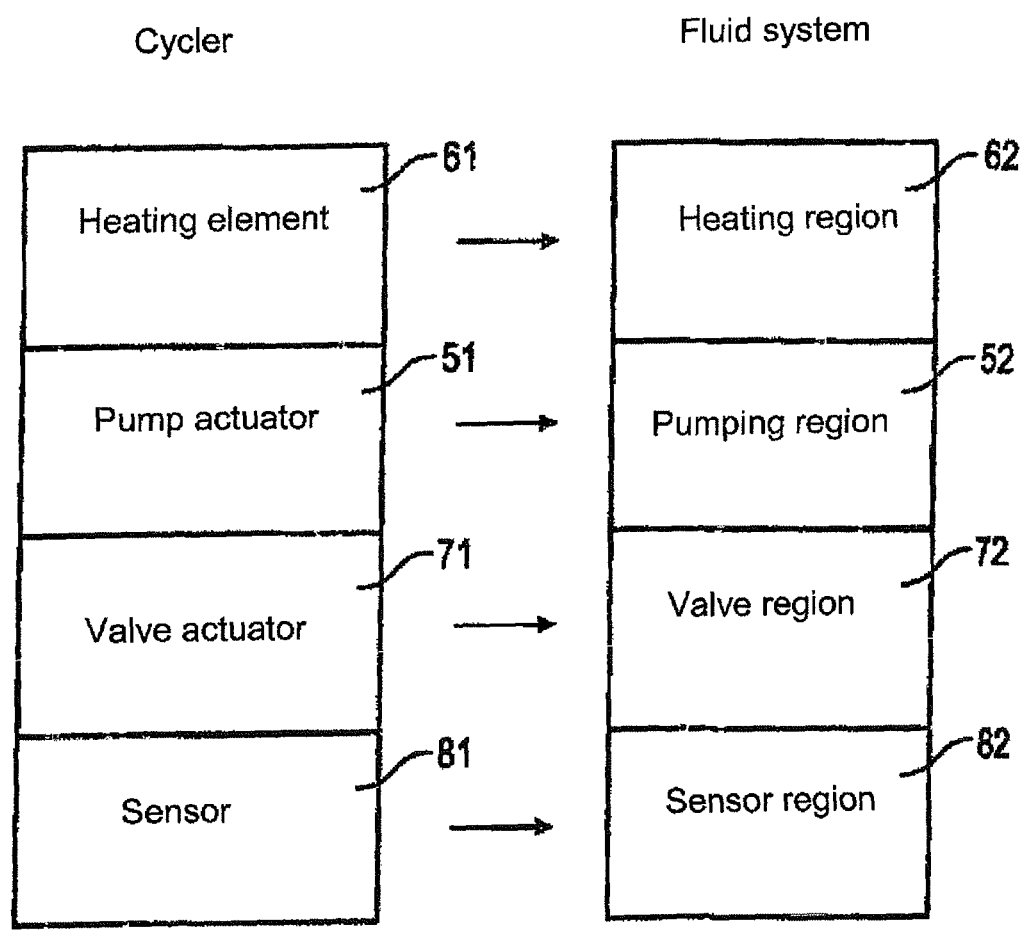
Figure 4A:
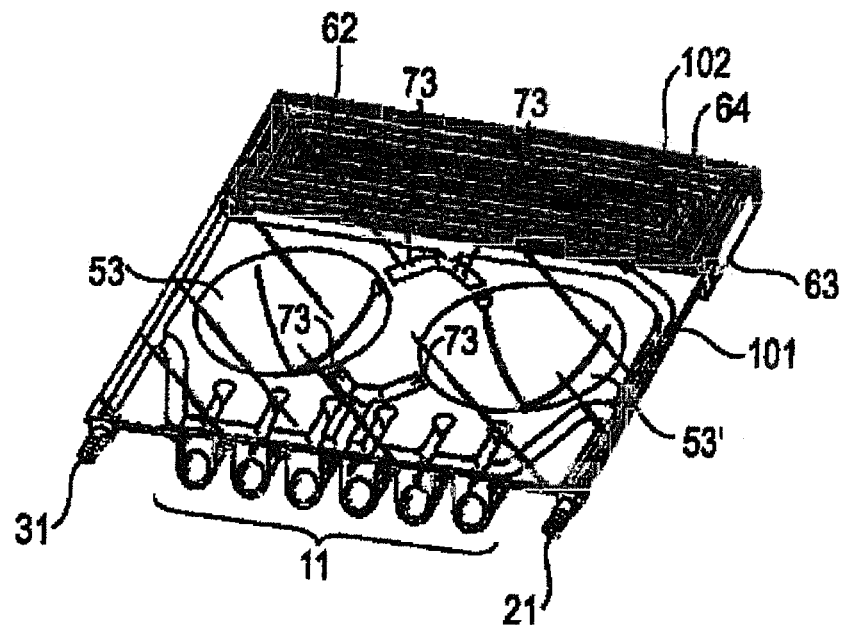
Figure 4B:
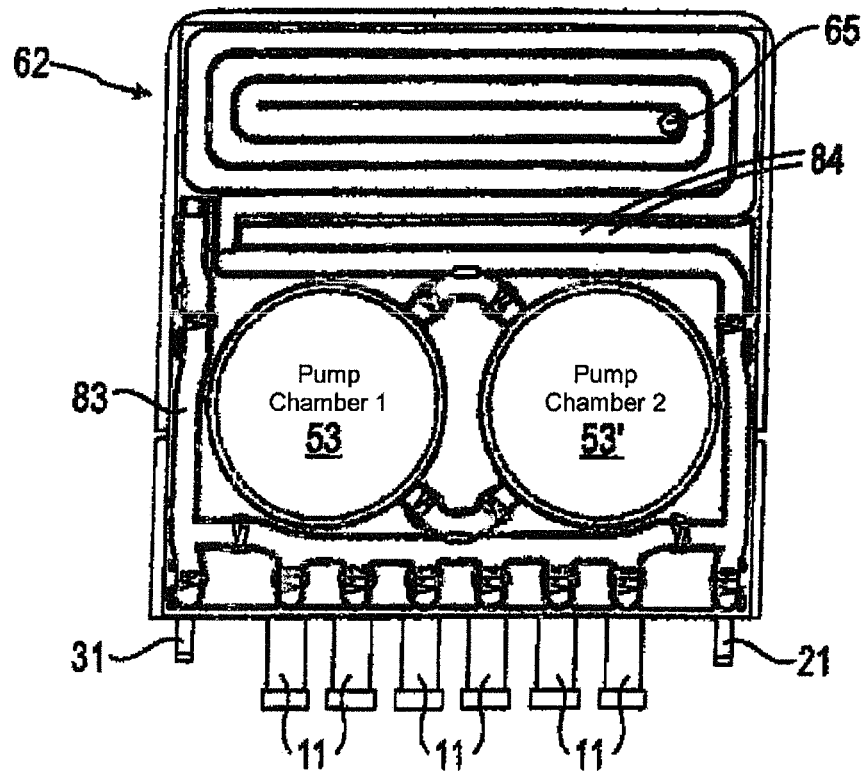
Figure 5:
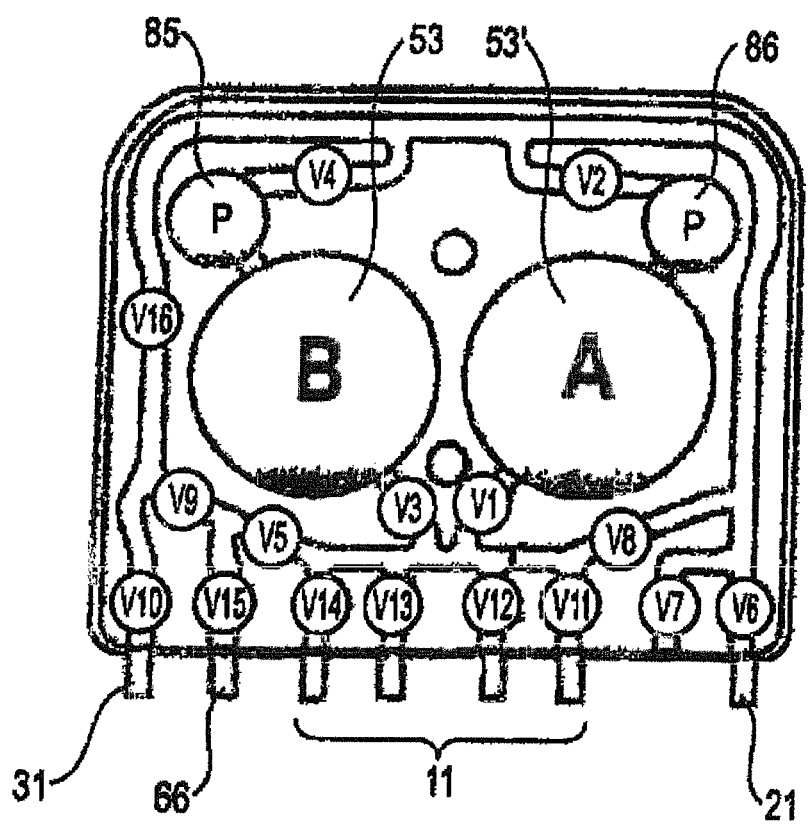
Figure 6:
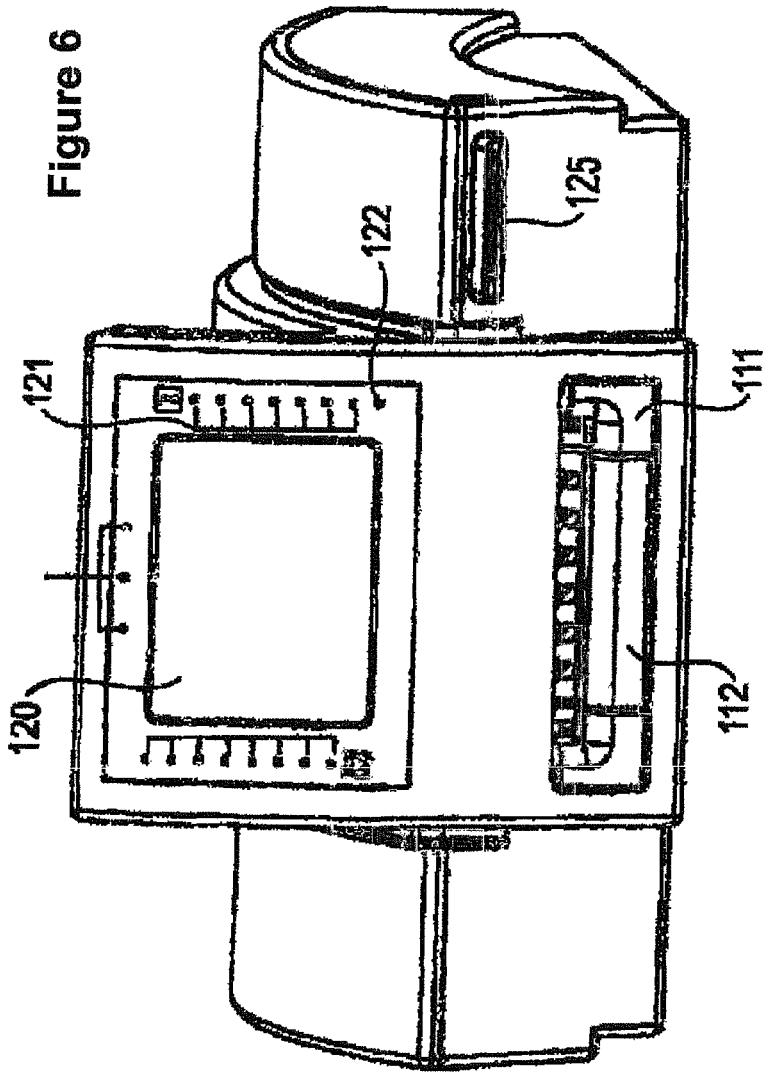
Figure 7:
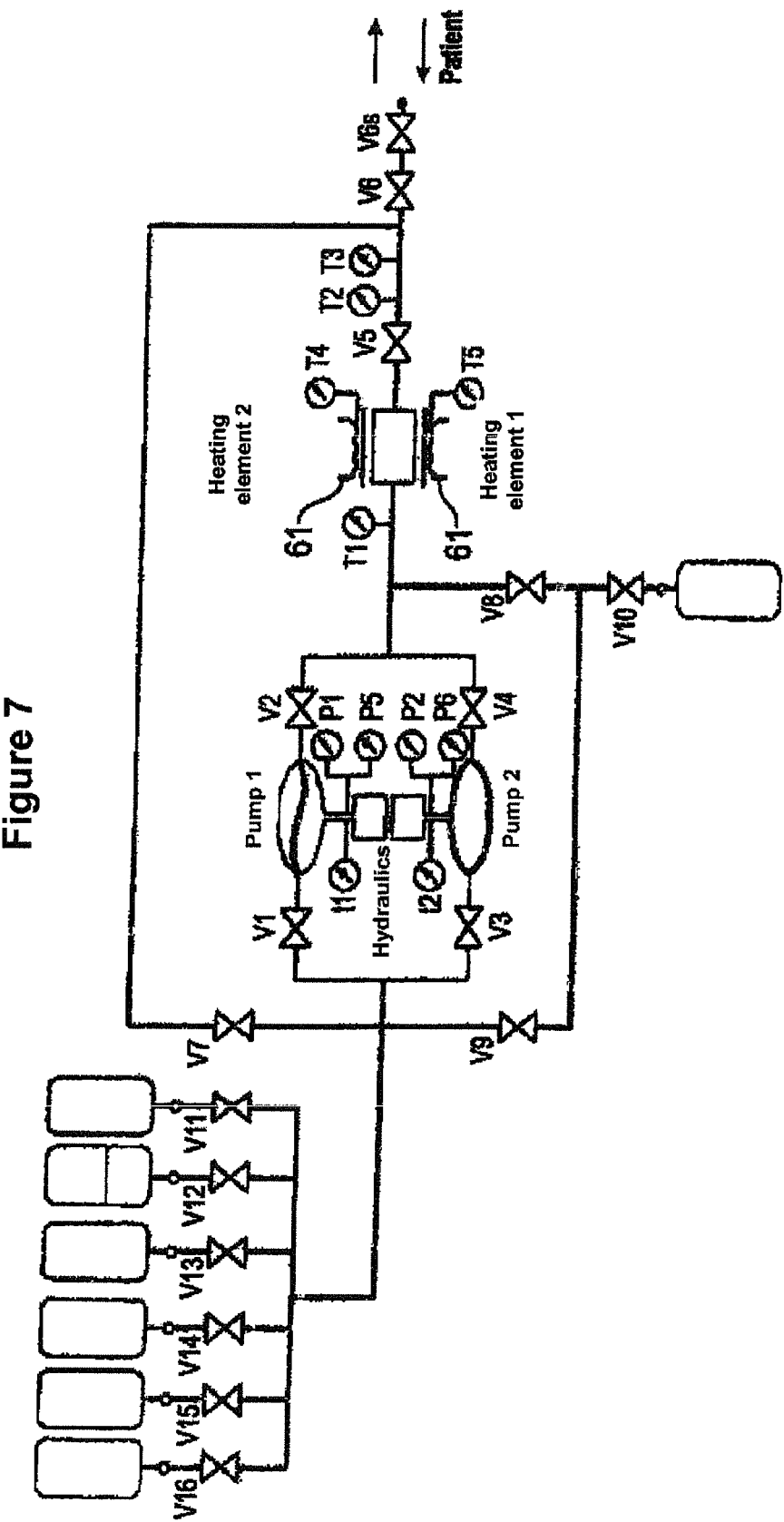
Figure 8:
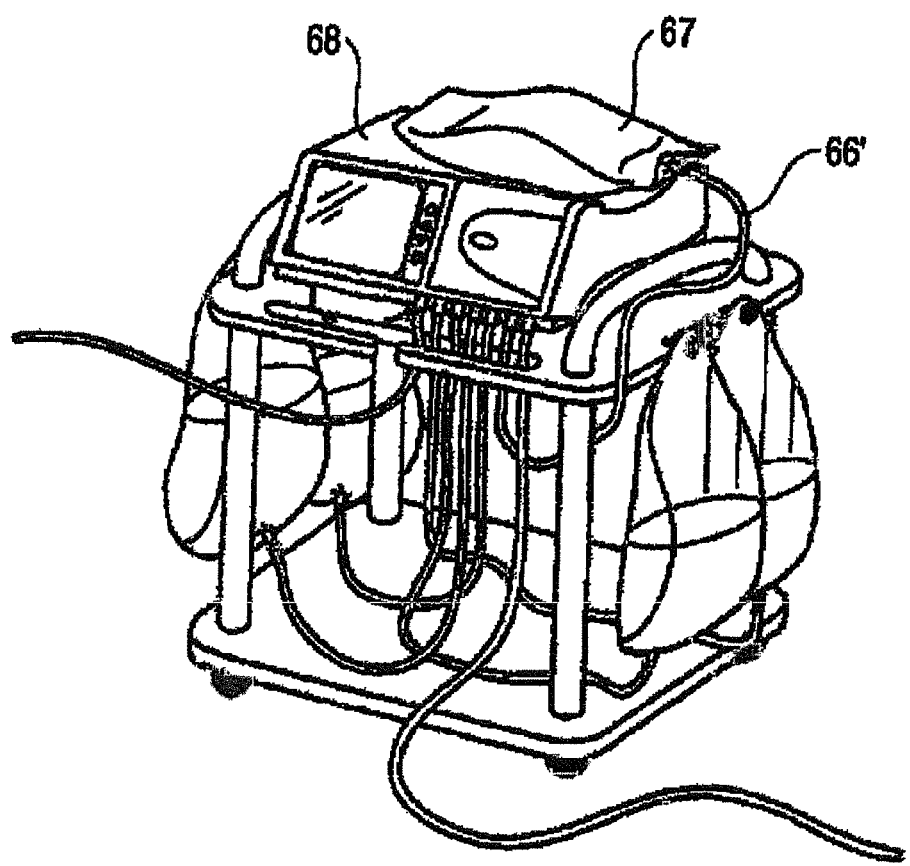
Figure 9:
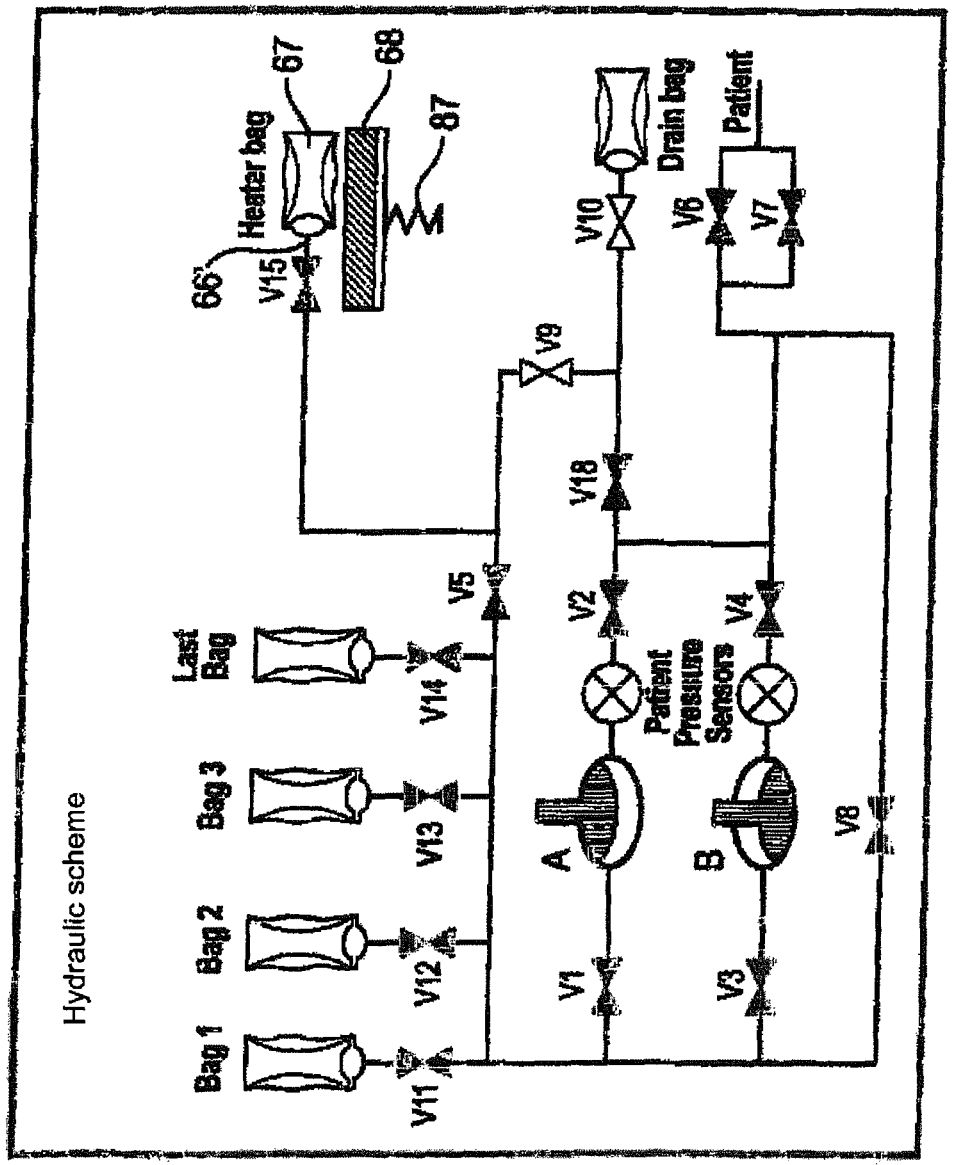
Figure 10:
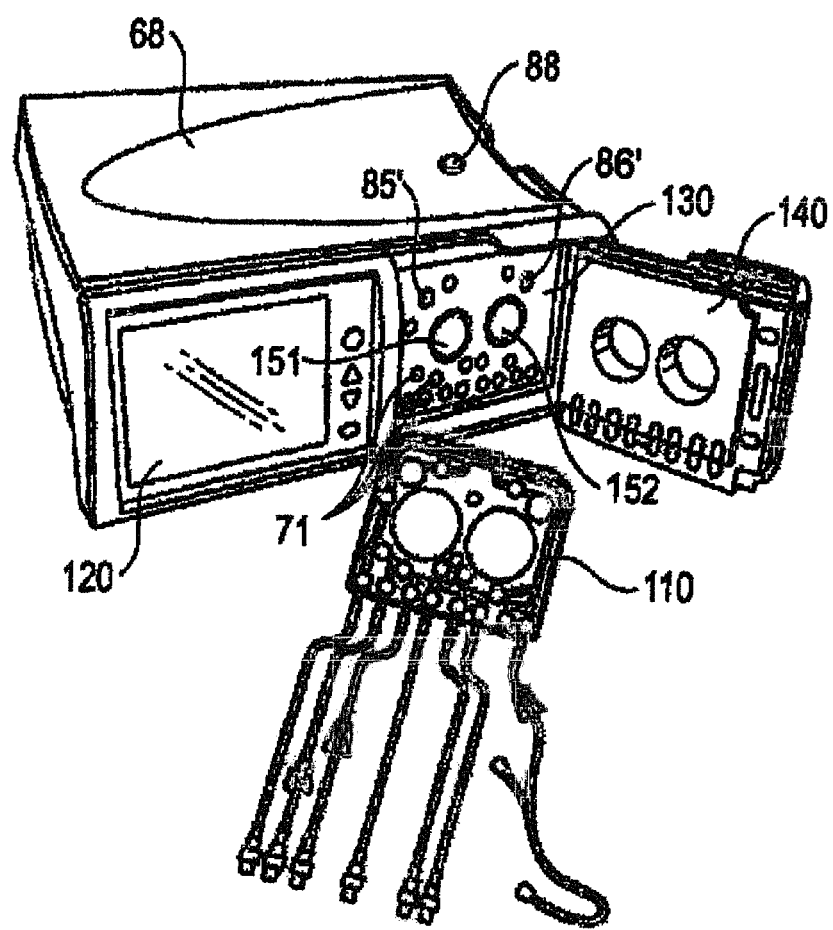
Figure 11:
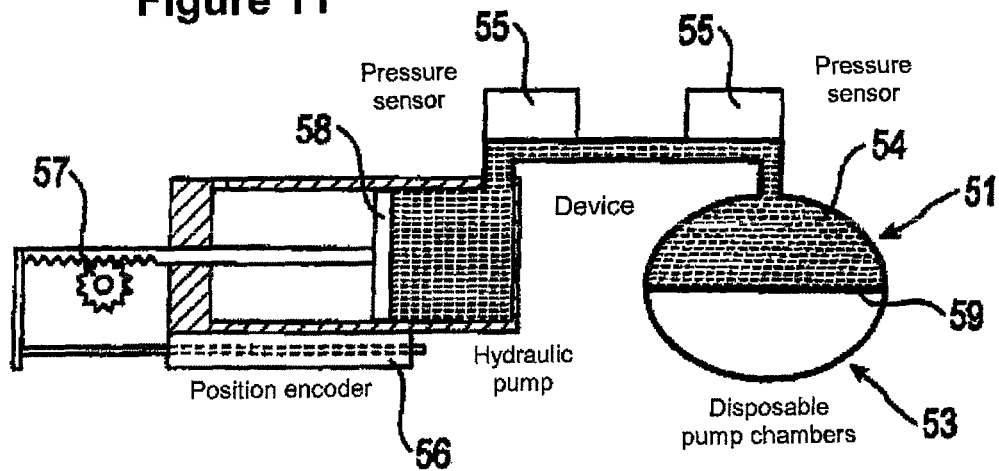
Figure 12A:
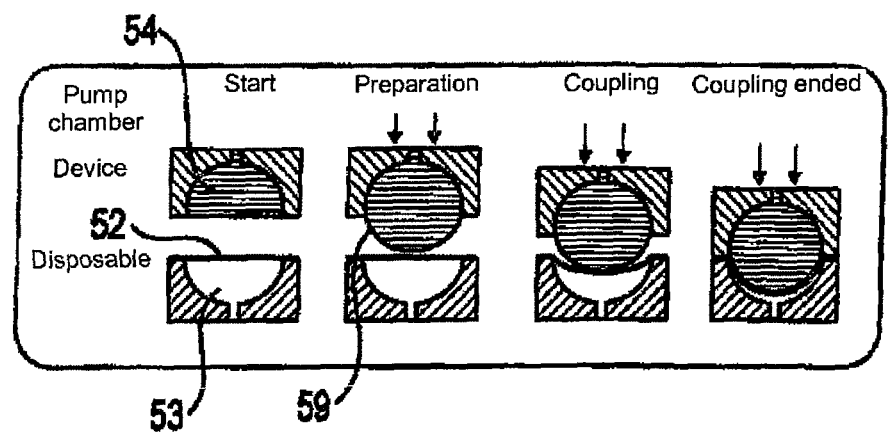
Figure 12B:
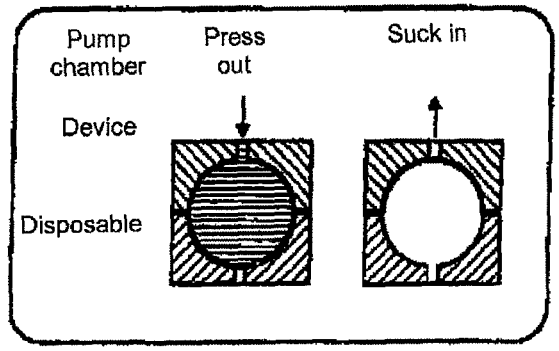

There are shown:

FIG. 1*a* a first diagram showing a first typical process of an automatic peritoneal dialysis treatment;

FIG. 1*b* a second diagram showing a second typical process of an automatic peritoneal dialysis treatment;

FIG. 1*c* a third diagram showing a third typical process of an automatic peritoneal dialysis treatment;

FIG. 2 a schematic diagram of a peritoneal dialysis system;

FIG. 3 a schematic diagram of the division of the peritoneal dialysis system into a dialysis machine and a fluid system;

FIG. 4*a* a perspective view of a first embodiment of a cassette;

FIG. 4*b* a top view of the first embodiment of a cassette;

FIG. 5 a second embodiment of a cassette;

FIG. 6 a perspective view of a first embodiment of a dialysis machine;

FIG. 7 a flowchart of a first embodiment of a peritoneal dialysis system;

FIG. 8 a perspective view of a second embodiment of a dialysis machine;

FIG. 9 a flowchart of a second embodiment of a peritoneal dialysis system;

FIG. 10 the coupling of the cassette in the second embodiment of a peritoneal dialysis system;

FIG. 11 a first embodiment of a pump actuator;

FIG. 12*a* a diagram showing four steps of a coupling method of a pumping region of the cassette to a pump actuator;

FIG. 12*b* a diagram showing two steps of a pumping method;

FIG. 13 a schematic diagram of the design of an embodiment of a controller; and

Figure 14A:
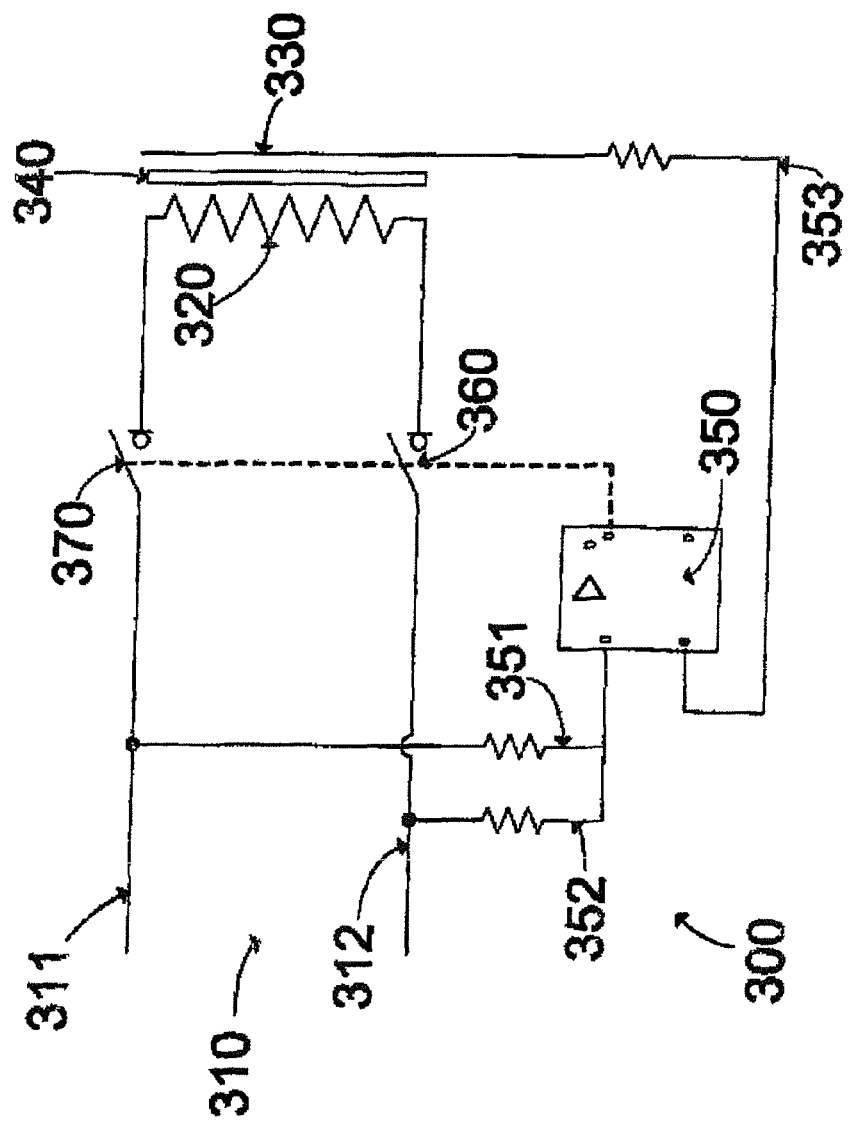
Figure 14B:
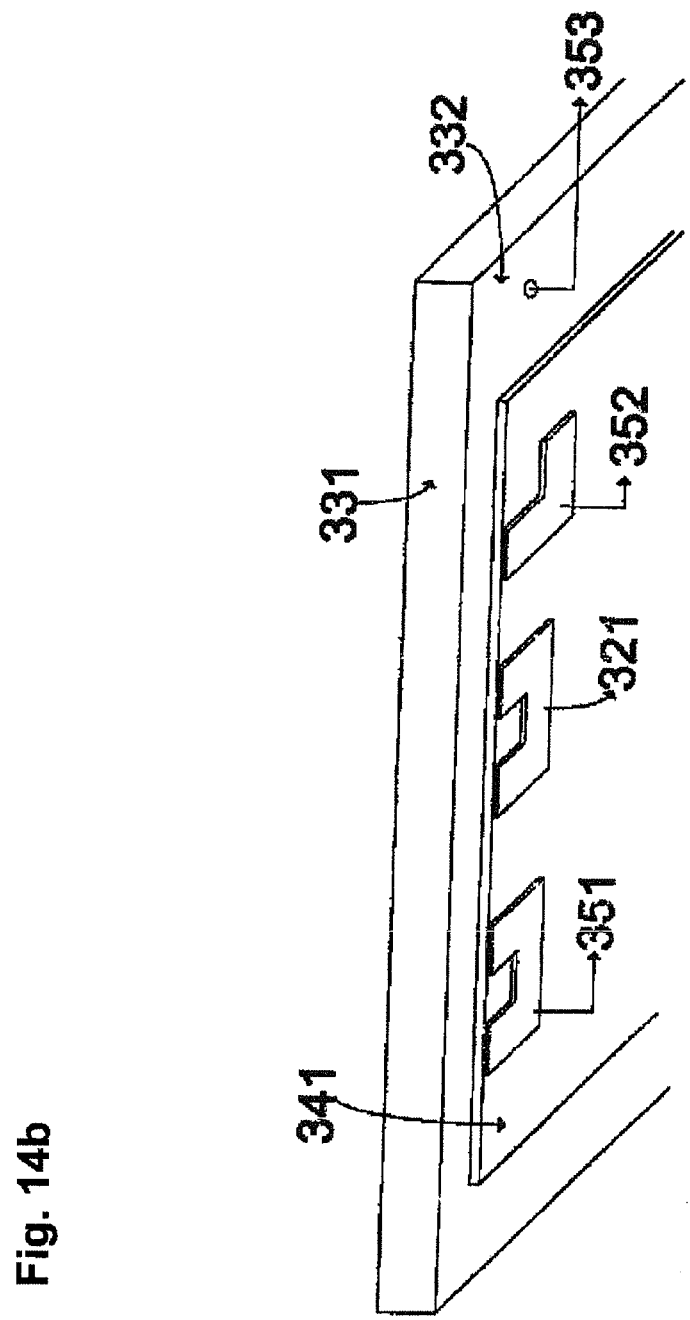
Figure 15:
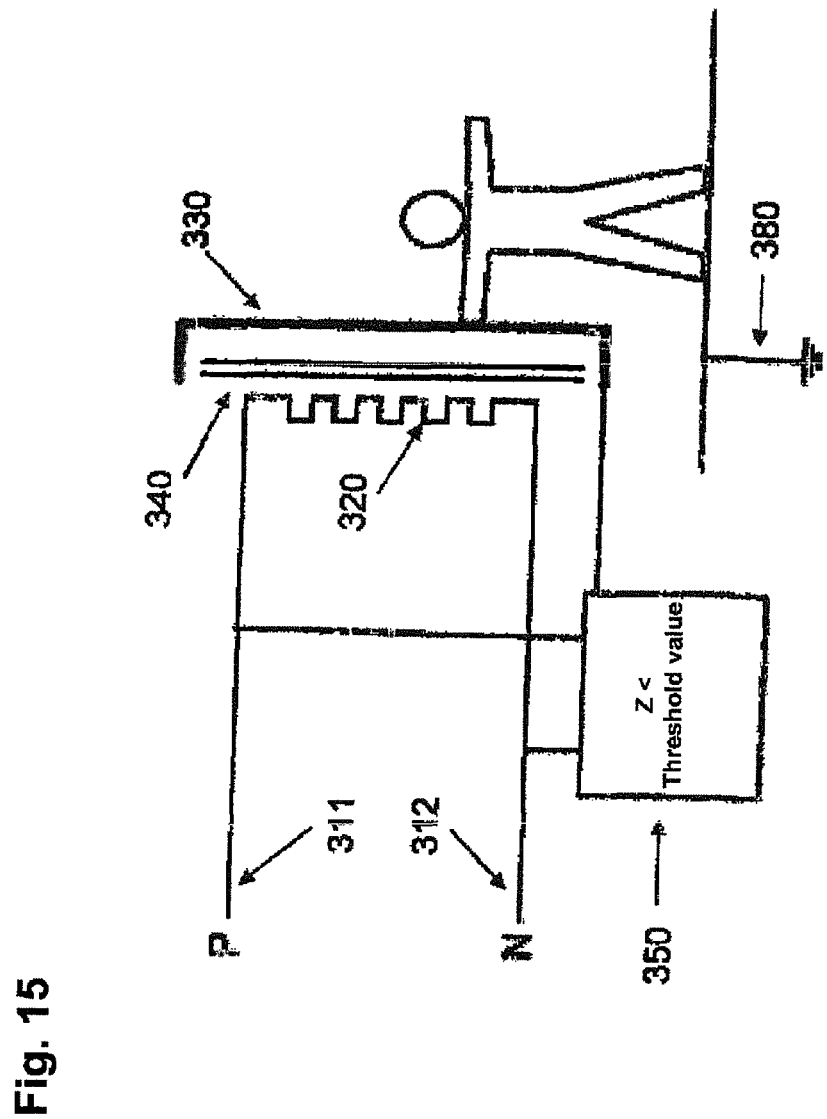
Figure 16:
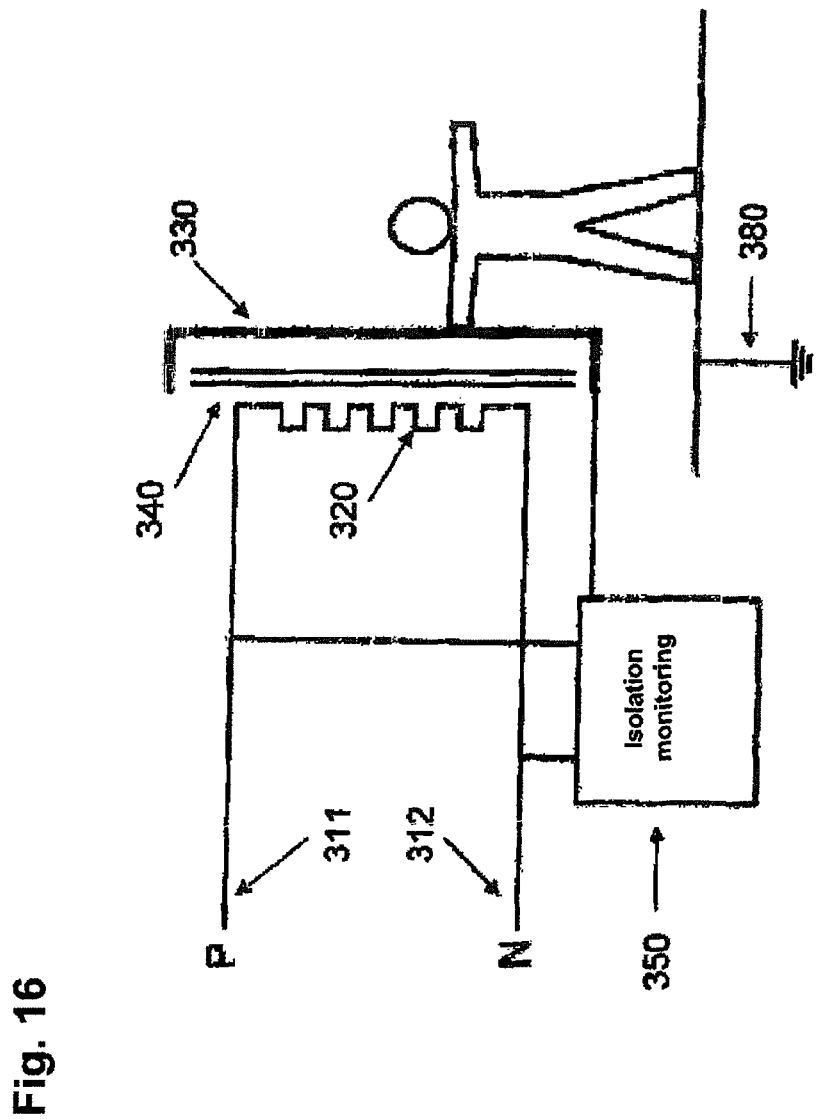
Figure 17:
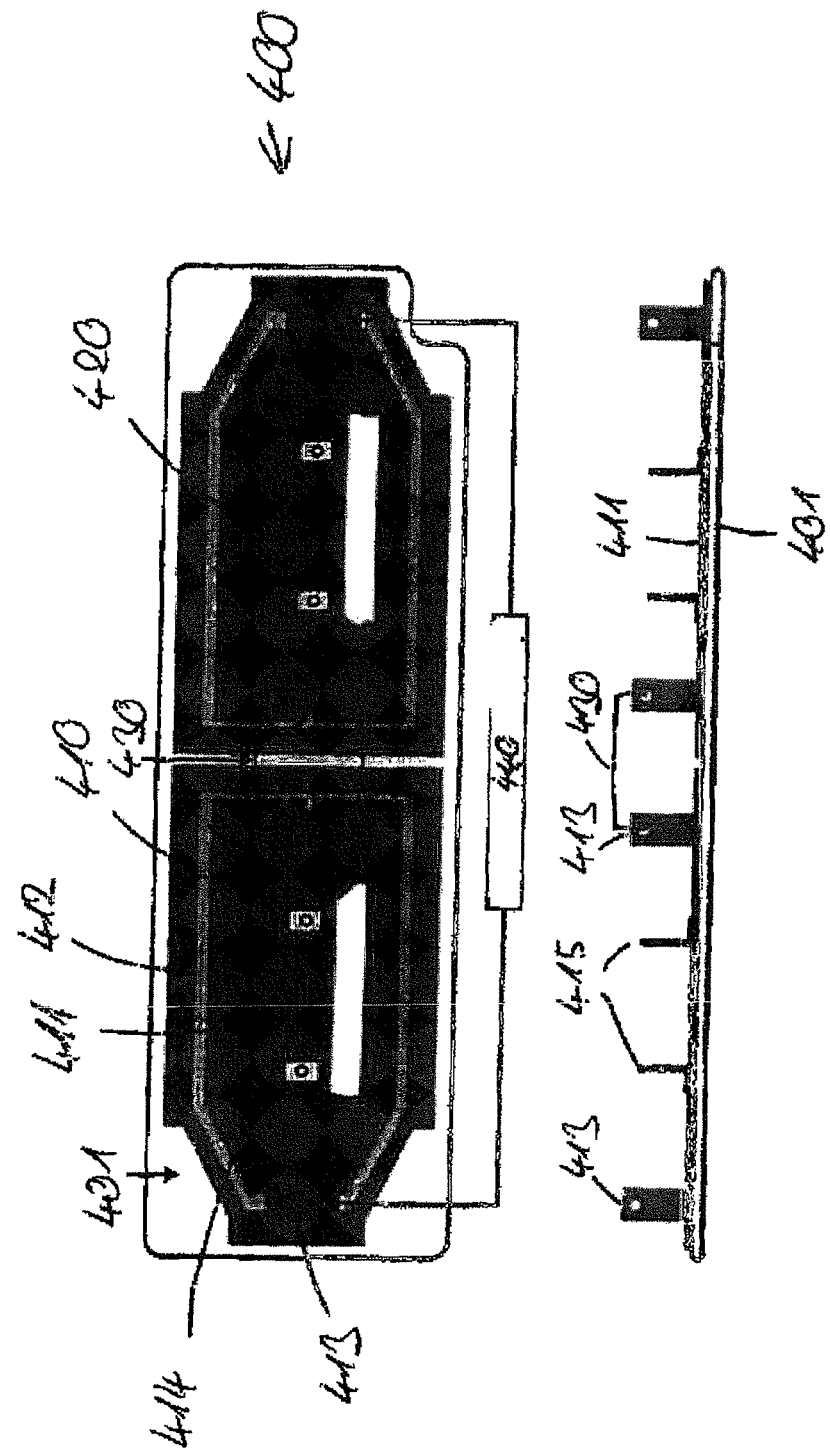

FIG. 14*a* a schematic of a device in accordance with the invention electrically operable via a mains voltage connection and having an insulation monitor;

FIG. 14*b* a partial section view through an embodiment of a live element of a device in accordance with the invention;

FIG. 15 a first embodiment of a device in accordance with the invention having an insulation monitor;

FIG. 16 a second embodiment of a device in accordance with the invention having an insulation monitor; and FIG. 17 an embodiment of an inventive medical device in accordance with the second aspect of the present invention having a heating element such as is arranged on a second ceramic layer.

The function of a dialysis machine in which the present invention is used will first be described generally in the following. The dialysis machine in this embodiment is in this respect a peritoneal dialysis machine. The components described below can, however, also be used in the same manner or in a similar manner for a hemodialysis machine.

Peritoneal dialysis is a variant of artificial hemodialysis in which the peritoneum of the patient which has a good blood supply is used as a filter membrane natural to the body. Dialysate is introduced into the abdominal cavity via a catheter for this purpose. In accordance with the principle of osmosis, urea components of the blood now diffuse through the peritoneum into the dialysate present in the abdominal cavity. After a specific dwell time, the dialysate with the urea components is again eliminated from the abdominal cavity.

In automatic peritoneal dialysis, a dialysis machine controls and monitors the introduction of the fresh dialysate into the abdominal cavity and the elimination of the consumed dialysate. Such a dialysis machine, also called a cycler, in this respect usually fills and voids the abdominal cavity several times overnight, i.e. while the patient is asleep.

In FIGS. 1a to 1c, three different method procedures are shown such as are carried out by a dialysis machine. One or more of these process procedures is in this respect usually stored in the controller of the dialysis machine. It is usually possible in this respect to adapt the stored process procedures to the patient.

In FIGS. 1a to 1c, the dialysate quantity V respectively present in the patient's abdominal cavity is entered over the time t. In this respect, FIG. 1a shows the development of a normal automatic peritoneal dialysis treatment overnight. At the start of the treatment, an initial outflow 5 first takes place in this respect through which dialysate which was left in the abdominal cavity of the patient over the day is removed. A plurality of treatment cycles 1 then takes place; in FIG. 1a, three sequential treatment cycles 1. Each treatment cycle in this respect comprises an inflow phase 2, a dwell phase 3 and an outflow phase 4. In this respect, a specific volume of fresh dialysate fluid is introduced into the patient's abdominal cavity during the inflow phase 2. The maximum permitted dialysate quantity in this respect amounts to between approximately 1.5 and 3 l depending on the patient. The fresh dialysate now remains in the abdominal cavity for a specific dwell time 3. The dwell phase in this respect typically lasts some hours. The now consumed dialysate is then removed from the abdominal cavity again in the outflow phase 4. A new treatment cycle then starts. The treatment is concluded with a last inflow 6 by which a specific quantity of fresh dialysate is introduced into the patient's abdominal cavity. It then remains in the patient's abdominal cavity over the day.

The individual treatment cycles 1 which take place overnight are in this respect automatically controlled by the controller of the dialysis machine. The initial outflow and the last inflow can likewise be controlled automatically by the dialysis machine. Alternatively, they are activated manually by an operator or by the patient.

A so-called tidal treatment is shown in FIG. 1b. This also starts with an initial outflow 5 and ends with a last inflow 6. A base cycle 7 is furthermore provided which is divided into a plurality of tidal cycles 8. In this respect, a base inflow phase 2' is initially provided. After the dwell phase 3, however, the complete dialysate volume is no longer removed from the abdominal cavity, but rather only a certain part quantity of the dialysate present in the abdominal cavity. This is then replaced by a corresponding volume of fresh dialysate. After a further dwell cycle, a further tidal removal can take place in which the total dialysate present in the abdomen is not removed. At the end of the base cycle 7, a base outflow phase 4' takes place in which the total dialysate is now removed. Only one base cycle 1 is in this respect shown in FIG. 1b. Alternatively, however, a plurality of base cycles can also be provided.

The course of a peritoneal dialysis treatment with a so-called PD plus treatment is shown in FIG. 1c. In this respect, a conventional peritoneal dialysis treatment takes place during the night 9 which can e.g. be carried out in accordance with the FIG. 1a or 1b. An additional PD plus treatment is, however, furthermore provided during the day in which the consumed dialysate is removed in an outflow phase 5' and is replaced by fresh dialysate in an inflow phase 6'. In the PD plus treatment, a normal night-time peritoneal dialysis treatment is combined with one or more additional treatment cycles during the day. The course of the night-time treatment is in this respect carried out as customary automatically by the dialysis machine. The treatment cycles during the day are likewise carried out and monitored via the machine.

The design of a typical peritoneal dialysis system is now shown schematically in FIG. 2. The peritoneal dialysis system in this respect includes a container 10 with fresh dialysate and an outflow 20 for used dialysate. A connector 30 is furthermore provided which can be connected to a catheter of the patient either to introduce fresh dialysate into the abdominal cavity of the patient or to remove consumed dialysate from the abdominal cavity. The container 10 with fresh dialysate, the outflow 20 for used dialysate and the connector 30 to the patient are in this respect connected to one another via fluid paths 100 and form the fluid system of the peritoneal dialysis system together with them.

A dialysis machine 40, also called a cycler, is provided for the carrying out of the peritoneal dialysis treatment. The dialysis machine 40 in this respect includes the following main components:

A pump 50 which is used for the transport of the fluids. The pump 50 in this respect conveys the fresh dialysate from the container 10 to the connector 30. The pump 50 can furthermore transport the consumed dialysate from the connector 30 to the outflow 20.

Valves 70 which are used for the control of the fluid flows. The valves 70 open and close the fluid paths 100 in order thus to establish the corresponding fluid connections between the container 10, the connector 30 and the outflow 20.

A heating 60 which brings the fresh dialysate to a temperature of approximately 37° C. before it is supplied to the patient. Since relatively large quantities of dialysate are supplied directly into the abdominal cavity of the patient in peritoneal dialysis, the heating 60 is necessary in order not to cool the patient too much and to avoid an unpleasant feeling by dialysate which is too cold.

Sensors 80 via which the proper procedure of the treatment can be monitored and/or controlled. Temperature sensors can in particular be used in this respect. Pressure sensors can furthermore optionally be used.

All the components of the dialysis machine 40 are in this respect controlled via a controller 90. In this respect, the controller 90 in particular controls the pump 50, the heating 60 and the valves 70 on the basis of the data of the sensors 80. The controller 90 in this respect provides the automatic procedure of the peritoneal dialysis. The controller 90 in this respect includes as an important component a balance 95 which balances the fluid quantities supplied to and removed from the patient. The balance in this respect prevents the patient from being given too much fluid or having too much fluid removed.

The balance 95 can in this respect take place solely on the basis of the control data and/or the sensor data for the pump 50. Alternatively, the balance can also take place via separately provided balancing chambers. It is equally possible to use scales for the balancing. Such scales, for example, weigh the weight of the container 10 with fresh dialysate and/or a container 20 with used dialysate.

Since the dialysate is dispensed to the patient directly into the abdominal cavity in peritoneal analysis, extreme sterility must be observed. The fluid paths or the fluid system which come into contact with the fresh dialysate and/or the used dialysate are therefore usually designed as disposable parts. The fluid paths or the fluid system are in this respect in particular designed as plastic parts. They can thus be supplied in a sterile outer packaging and only unpacked briefly before the treatment.

In order nevertheless to enable a control of the peritoneal dialysis by the dialysis machine 40, the fluid system has to be coupled to the dialysis machine 40. In this respect, it is shown schematically in FIG. 3 how individual elements of the dialysis machine 40 are coupled to corresponding regions of the fluid system.

The dialysis machine 40 in this respect has a heating element 61. This must be coupled to a corresponding heating region 62 of the fluid system. The coupling in this respect enables the transfer of thermal energy from the heating element 61 to the dialysate present in the heating region 62.

The dialysis machine 40 furthermore has one or more pump actuators 51 which are coupled to a pump region 52 of the fluid system. The pump actuators 51 in this respect generate a pump force which is transferred to the pump region 52. The liquid present in the pump region 52 can hereby be moved along the fluid paths.

The dialysis machine furthermore has one or more valve actuators 71. They generate a closing movement which is transferred to corresponding valve regions 72 of the fluid paths. The valve regions 72 of the fluid paths can hereby be correspondingly closed or opened.

The dialysis machine furthermore has one or more sensors 81. They are coupled to a corresponding sensor region 82 of the fluid system. The sensors 81 can hereby measure specific properties of the dialysate. The temperature of the dialysate can in particular be measured hereby. Provision can furthermore be made that the pressure in the fluid system is determined.

The dialysis machine naturally optionally has further actuators and/or sensors which do not have to be coupled to the fluid paths.

The individual components of a peritoneal dialysis system should now be presented in more detail in the following with reference to embodiments.

1. Fluid System 1.1 Dialysis Container

Fresh dialysate is usually provided in plastic bags. Such plastic bags usually have two layers of plastic film which are welded to one another in a marginal region and thus form a container which is filled with fresh dialysate. A hose element is usually welded to this container by which the dialysate can be removed from the bag. A connector is usually arranged at the hose element via which the dialysate container can be connected to the other fluid paths. The bag furthermore usually has a cut-out or eyelet at the side disposed opposite the hose and the bag can be hung onto a hook by it. It can hereby be ensured that the dialysate flows out of the bag without problem.

The dialysate usually comprises a buffer, an osmotic agent and electrolytes. Bicarbonate can e.g. be used as the buffer in this respect. Glucose is usually used as the osmotic agent. Alternatively, glucose polymers or glucose polymer derivatives can also be used. The electrolytes usually include calcium and sodium.

The dialysate can be heat sterilized in this respect. This advantageously takes place after the dialysate has been filled into the bag. Both the dialysate and the bag are hereby heat sterilized. In this respect, the filled bag is usually first packed into an outer packaging, whereupon the total system is sterilized.

Since the finished dialysate solution can often not be heat sterilized or cannot be stored for a long time in dependence on the ingredients, provision can be made to store individual components of the dialysate separately and only to combine them shortly before the treatment. A first individual solution in this respect usually includes the buffer, while a second individual solution includes glucose and electrolytes. Optionally, more than two individual solutions, and thus more than two regions, can also be provided in a bag. In this respect, a multi-chamber bag, in particular a double-chamber bag, can be provided which has a plurality of separate regions for the storage of the individual solutions. These regions are separated by a connection element which can be opened mechanically to mix the individual solutions with one another. A so-called peel seam can in particular be provided between the two regions of the bag in this respect and opens on the application of a specific pressure to at least one of the regions of the bag.

Since relatively large quantities of dialysate are consumed during a night-time peritoneal dialysis treatment, a plurality of dialysate containers are usually used in parallel. They are connected to the fluid paths via corresponding connectors and can be used for the filling of the patient by a corresponding connection of the valves.

1.2 Outflow

For the disposal of the consumed dialysis fluid, it can either be led off immediately into the drainage system or first be collected in an outflow container. A bag is usually likewise used as an outflow container in this respect. It is empty before the start of the treatment and can thus take up the consumed dialysate. The bag can then be correspondingly disposed of after the end of the treatment.

1.3 Cassette

As already initially described, the fluid system has a plurality of regions in which the dialysis machine has to have an effect on the fluid system. The fluid system has to be coupled to the dialysis machine for this purpose.

Cassettes are used to simplify the coupling of the fluid paths to the dialysis machine and the effect of the corresponding elements of the dialysis machine on the fluid paths. A plurality of regions in which the dialysis machine has an effect on the fluid paths are jointly arranged in such a cassette. For this purpose, a cassette usually has a hard part of plastic into which chambers open to one side are introduced as fluid paths. These chambers are covered by a flexible plastic film which provides the coupling to the dialysis machine. The flexible plastic film is in this respect usually welded to the hard part in a marginal region. The cassette is pressed with a coupling surface of the dialysis machine so that the actuators and/or sensors of the dialysis machine come into contact with corresponding regions of the cassette.

The cassette furthermore has connections for the connection of the dialysate container 10, of the connector 30 as well as of the outflow 20.

A cassette in this respect usually includes at least one pump region and one or more valve regions. The liquid transport can thus be controlled by the fluid system via the cassette. The cassette can furthermore have sensor regions which enable a simple coupling of sensors of the dialysis machine to the fluid system. The cassette can optionally furthermore have one or more heating regions which can be coupled to corresponding heating elements of the dialysis machine.

A first embodiment of a cassette is shown in FIGS. 4a and 4b. It has a hard part 101 of plastic in which the fluid paths and coupling regions are introduced as corresponding cut-outs, chambers and passages. The hard part can in this respect be produced e.g. as an injection molded part or as deep drawn part. The coupling plane of the hard part 101 is covered by a flexible film 102 which is welded to the hard part in a marginal region. The flexible film 102 is pressed with the hard part by the pressing of the cassette with a coupling surface of the dialysis machine. The fluid paths within the cassette are separated from one another in a fluid tight manner by the pressing of the flexible film with the web regions of the hard part.

The cassette has connections for the connection of the cassette to the other fluid paths. On the one hand, a connection 21 is provided for the connection to the outflow 20 as well as a connection 31 for the connection to the connector 30. Corresponding hose elements which are not shown in FIG. 4a can be provided at these connections. The cassette furthermore has a plurality of connections 11 for the connection of dialysate containers 10. The connections 11 are in this respect designed in the first embodiment as connectors to which corresponding connector elements can be connected.

The connections are in each case in connection with fluid paths within the cassette. Valve regions are provided in these fluid paths. In these valve regions, the flexible film 102 can be pressed into the hard part 101 via valve actuators at the machine side such that the corresponding fluid path is blocked. The cassette in this respect first has a corresponding valve for each connection via which this connection can be opened or closed. The valve V10 is in this respect associated with the connection 21 for the outflow 20; the valve V6 is associated with the connection 31 for the patient connector 30. The valves V11 to V16 are associated with the connections 11 for the dialysate container 10.

Pump chambers 53 and 53' are furthermore provided in the cassette via which corresponding pump actuators of the dialysis machine can be actuated. The pump chambers 53 and 53' are in this respect concave cut-outs in the hard part 101 which are covered by the flexible film 102. The film can now be pressed into the pump chambers 53 and 53' or pulled out of these pump chambers again by pump actuators of the dialysis machine. A pump flow through the cassette can hereby be generated in cooperation with the valves V1 to V4 which connect the accesses and outflows of the pump chambers 53 and 53' and are designated by the reference numeral 73 in FIG. 4a. The pump chambers can in this respect be connected via corresponding valve circuits to all connections of the cassette.

A heating region 62 is furthermore integrated into the cassette. In this region, the cassette is brought into contact with heating elements of the dialysis machine which heat the dialysate flowing through this region of the cassette. The heating region 62 in this respect has a passage for the dialysate which extends spirally over the heating region 62. The passage is in this respect formed by webs 64 of the hard part which are covered by the flexible film 102.

The heating region 62 is in this respect provided at both sides of the cassette. A flexible film is also arranged at the hard part in the heating region at the lower side 63 of the cassette for this purpose. The flexible film is in this respect also welded to the hard part in a marginal region. A passage is likewise arranged at the lower side and the dialysate flows through it. The passages on the lower side and on the upper side are in this respect formed by a middle plate of the hard part which separates the upper side from the lower side and on which webs are downwardly and upwardly provided which form the passage walls. In this respect, the dialysate first flows spirally on the upper side up to the aperture 65 through the middle plate from where the dialysate flows back at the lower side through the corresponding passage. The heating surface which is available for the heating of the fluid can be correspondingly enlarged by the heating region provided at the upper side and at the lower side. An embodiment of the cassette is, however, naturally also possible in which a heating region is only arranged on one side of the cassette.

Embodiments of the cassette are furthermore possible in which a heating element is integrated into the cassette. An electrical heating element such as a heating coil can in this respect in particular be cast into the hard part of the cassette. A heating element on the machine side can thus be dispensed with and the throughflow heating can be integrated into the cassette. In this respect, electrical contacts are arranged at the cassette for the connection of the electrical heating element.

The cassette furthermore has sensor regions 83 and 84 by which temperature sensors of the dialysis machine can be coupled to the cassette. The temperature sensors in this respect lie on the flexible film 102 and can thus measure the temperature of the liquid flowing through the passage disposed below. Two temperature sensors 84 are in this respect arranged at the inlet of the heating region. A temperature sensor 83 via which the temperature of the dialysate pumped to the patient can be measured is provided at the outlet at the patient side.

A second embodiment for a cassette is shown in FIG. 5. The cassette in this respect substantially corresponds in its design to the first embodiment, but does not include any heating region. On the use of this cassette, the heating therefore does not take place as shown in the first embodiment via a heating region integrated into the cassette, but rather e.g. via a heating bag which is placed onto a heating plate of the dialysis machine.

The second embodiment of a cassette shown in FIG. 5 in turn has fluid paths which can be opened and closed via valve regions which are here likewise numbered consecutively from V1 to V16. The cassette furthermore has connections for the connection to further components of the fluid system. In this respect, the connection 21 is in turn provided for the connection to the outflow 20 and the connection 31 for connection to the connector 30 to the patient. Connections 11 are furthermore provided for the connection of dialysate containers 10.

Unlike the first embodiment, the cassette shown in the second embodiment has a further connection 66 for the connection of a heating bag. In this respect, the liquid can be pumped into a heating bag via the connection 66 for the heating of the fluid from the dialysate containers 10. This heating bag lies on a heating element so that the fluid present in the heating bag can be heated. The fluid is thereupon pumped from the heating bag to the patient.

The pump chambers 53 and 53' and the valves V1 to V4 correspond in design and function to the corresponding components in the first embodiment.

Unlike the first embodiment, the cassette in the second embodiment does not have any sensor region for the connection of a temperature sensor. It is rather arranged in the region of the heating elements. The cassette, however, has measurement regions 85 and 86 for the measurement of the pressure in the pump chambers 53 and 53'. The measurement regions 85 and 86 are in this respect chambers which are in fluid communication with the pump chambers and are likewise covered by the flexible film. Pressure sensors at the apparatus side which measure the pressure in the measurement chambers 85 and 86 and thus in the pump chambers 53 and 53' can be coupled to the measurement regions.

The connection of the connections 11, 21, 31 and 66 of the cassette to the further components of the fluid system takes place via hose connections in the second embodiment. Connectors are optionally arranged at these hose connections.

1.3 Hoses

The connection between the individual containers of the system, the cassette and the patient connector usually takes place via hose connections. Since they are in each case disposable articles, the hoses are in this respect usually already fixedly connected at at least one side to a further element. Hoses can e.g. already be provided at one or more of the connections of the cassette. Hoses can likewise already be in fixed communication with bags.

1.4 Connections

The fluid system is usually divided into a plurality of parts and packaged in sterile form in each case. These parts first have to be connected to one another for the treatment. The cassette and the dialysate bag or bags are in this respect in particular packaged separately from one another.

The connections between the individual elements of the fluid system usually take place via connectors. The connectors are in this case designed so that they enable a sterile connection between the individual components. This takes place e.g. via corresponding protective films which are automatically opened on the closing of the connector.

The connection of the individual components can in this respect take place manually by an operator or by the patient him or herself. Provision can alternatively be made that the connection of the individual components takes place by the dialysis machine.

For this purpose, the corresponding connectors can e.g. be placed into a connector receiver of the dialysis machine and can be automatically joined together by the dialysis machine.

An electronic control can furthermore be provided which monitors that the correct components of the system are connected to one another. Identification means such as barcodes or RFIDs which identify the components can be provided at the connectors for this purpose. The dialysis machine in this respect includes an identification means detection unit such as a barcode reader or an RFID detection unit which detects the identification means on the connectors. The controller of the peritoneal dialysis can hereby recognize whether the correct connectors were inserted.

Such a check of the correct assembly of the fluid system can in this respect in particular be combined with an automatic connection of the connectors. The system thus first checks whether the correct connectors were placed into the connector receivers. The connection between the connectors is only established by the dialysis machine when the correct connectors were inserted. Otherwise, the dialysis machine draws the attention of the user to the fact that the wrong connectors have been inserted.

2. The Dialysis Machine

The individual components of a dialysis machine should now be described in more detail in the following with reference to two embodiments.

A first embodiment of a dialysis machine is shown in this respect in FIG. 6 in which the first embodiment of a cassette is used. The peritoneal dialysis system resulting from the first embodiment of a dialysis machine and the first embodiment of a cassette is shown in FIG. 7 in this respect.

A second embodiment of a dialysis machine is shown in FIG. 8 in which the second embodiment of a cassette is used. The dialysis system resulting from the combination of the second embodiment of a dialysis machine and of the second embodiment of a cassette is then shown in FIG. 9.

The two embodiments differ in this respect, on the one hand, in the design of the heating, in the coupling between the dialysis machine and the cassette and in the design of the actuators and sensors.

2.1 Heating

The fresh dialysate has to be brought to body temperature before it is conveyed into the abdomen of the patient. The dialysis machine has a corresponding heating for this purpose.

The heating in this respect usually takes place via one or more heating elements. The heating elements can in this respect e.g. be ceramic heating elements. With such ceramic heating elements, a resistance strip is applied to a ceramic carrier. The resistance strip is heated by the application of a voltage to it, whereby the ceramic carrier material is also heated. The ceramic heating element is in this respect usually arranged on a heating plate. It can be made of aluminum, for example. The fluid paths are in turn coupled to the heating plate so that the dialysate present in the fluid paths can be heated.

Two different designs are available for the heating of the fluid. On the one hand, a larger quantity of dialysate can first be heated which is only pumped to the patient after the heating phase. This usually takes place via a heating bag which is placed on a heating plate of the dialysis machine.

The heating bag can in this respect be the dialysis bag in which the dialysate is provided. Usually, however, a separate heating bag is used in which the dialysate is pumped for heating. If the dialysate is heated in the heating bag, it is pumped to the patient from there.

Such a concept is realized in the second embodiment of a dialysis machine shown in FIGS. 8 and 9. In this respect, a heating bag 67 is provided which lies on a heating plate 68. The heating plate 68 is in this respect arranged on the upper side of the peritoneal dialysis machine so that it is easily accessible. The heating bag 67 is in this respect connected to the cassette via a line 66'. The cassette in this respect has the valves V5, V9 and V15 via which the heating bag 67 can be connected to the other components of the fluid system. Fresh dialysate can thus be pumped from the dialysate containers 10 via the pump chambers to the heating bag 67. At the start of a treatment, the heating bag 67 is therefore first filled with cold dialysate. The dialysate in the heating bag 67 is then heated to body temperature via the heating plate 68. The dialysate is thereupon pumped to the patient via the pump chambers. The heating bag 67 can thereupon be filled again so that the dialysate quantity required for the next treatment cycle can be heated.

A temperature sensor 88, which is in contact with the heating bag 67 and can thus measure the temperature of the dialysate in the heating bag 67, is advantageously provided in the region of the heating plate 68 in this respect. A temperature sensor can furthermore be provided at the heating plate or at the heating element which measures the temperature of the heating element or of the heating plate. A corresponding controller now makes sure that the heating plate does not become too hot for the material of the bag.

The heating bag 67 can additionally take over functions in the balancing of the fluid flows. The heating plate 68 can thus be part of scales 87 via which the weight of the heating bag 67 can be determined. The fluid quantity which is supplied to the patient after heating can hereby be determined.

Alternatively to the heating of the dialysate via a heating bag shown in the second embodiment, the dialysate can also be heated while it is being pumped to the patient. The heating thus works in the form of a continuous-flow water heater which heats the dialysate moved through the fluid system while it is being pumped through the fluid paths.

In this concept, a dialysate passage is provided which is coupled to a heating element of the dialysis machine. While the dialysate flows through the dialysate passage, it takes up heat from the heating element of the dialysis machine while so doing.

Such a concept is implemented in the first embodiment of a dialysis machine which is shown in FIGS. 6 and 7. The heating region is integrated in the cassette in this respect, as was already shown above. On the coupling of the cassette to the dialysis machine, the heating region of the cassette comes thermally into contact with heating elements of the dialysis machine.

The heating elements can in this respect likewise be designed as ceramic heating elements and can be in contact with heating plates which are the coupled to the heating region of the cassette. As already shown with respect to the cassette, a respective heating plate which heats the dialysate flowing through the heating region is in this respect in contact both with the upper side and with the lower side of the heating region.

Respective temperature sensor regions are provided in the cassette at the inflow and at the outflow of the heating region and come into contact with temperature sensors of the peritoneal dialysate by the coupling of the cassette. The temperature of the dialysate flowing into the heating region and the temperature of the dialysate flowing out of the heating region can thus be determined by the temperature sensors T1 to T3. Temperature sensors T4 and T5 are furthermore provided which determine the temperature of the heating elements and/or of the heating plates.

The use of at least two heating elements in this respect makes it possible to connect the heating elements to one another in each case such that they output substantially the same power at a supply voltage of 220 V as with a supply voltage of 110 V. For this purpose, the two heating elements are operated in a parallel circuit at 110 V, whereas they are operated in a series circuit at a supply voltage of 220V. Such an adaptation of the connection of the heating elements to the supply voltage can in this respect be implemented independently of whether the heating takes place in accordance with the first or the second embodiment.

2.2 Coupling the Cassette

To enable a coupling of the actuators and/or sensors of the dialysis machine to the corresponding regions of the cassette, the dialysis machine has a cassette receiver with a coupling surface to which the cassette can be coupled. The corresponding actuators, sensors and/or heating elements of the dialysis machine are arranged at the coupling surface. The cassette is pressed with this coupling surface such that the corresponding actuators, sensors and/or heating elements come into contact with the corresponding regions in the cassette.

In this respect, a mat of a flexible material, in particular a silicone mat, is advantageously provided at the coupling surface of the dialysis machine. It ensures that the flexible film of the cassette is pressed with the web regions of the cassette and thus separates the fluid paths within the cassette.

A peripheral margin of the coupling surface is furthermore advantageously provided which is pressed with the marginal region of the cassette. The pressing in this respect advantageously takes place in an airtight manner so that an under-pressure can be built up between the coupling surface and the cassette.

A vacuum system can optionally also be provided which can pump air out of the space between the coupling surface and the cassette. A particularly good coupling of the actuators, sensors and/or heating elements of the peritoneal dialysis device with the corresponding regions of the cassette is hereby made possible. In addition, the vacuum system allows a leak tightness check of the cassette. A corresponding vacuum is applied after the coupling for this purpose and a check is made whether this vacuum is maintained.

The pressing on of the cassette takes place pneumatically, for example. For this purpose, usually an air cushion is provided which is filled with compressed air and thus presses the cassette onto the coupling surface.

The cassette receiver usually has a receiver surface which is disposed opposite the coupling surface and into which the hard part of the cassette is inserted. The receiver surface advantageously has corresponding recesses for this purpose. The receiver surface with the inserted cassette can then be pressed onto the coupling surface via a pneumatic pressing apparatus.

The insertion of the cassette can in this respect take place in different manner. In the first embodiment of a dialysis machine which is shown in FIG. 6, a drawer 11 is provided for this purpose which can be moved out of the dialysis machine. The cassette is inserted into this drawer. The cassette is then pushed into the dialysis machine together with the drawer. The pressing of the cassette with the coupling surface which is arranged in the interior of the apparatus thereupon takes place. In this respect, the cassette and the coupling surface are first moved mechanically toward one another and then pressed with one another pneumatically.

The coupling of a cassette 110 in accordance with the second embodiment is shown in more detail in FIG. 10. The coupling surface 130 is freely accessible by opening a door 140 so that the cassette can be arranged at the correct position at the coupling surface 130. The coupling surface 130 is in this respect inclined rearwardly toward the vertical, which enables an easier coupling. The door 140 can now be closed so that a receiver surface at the door comes into contact with the rear side of the cassette. The pressing now takes place by an air cushion arranged at the door. In addition, a vacuum is applied between the coupling surface and the cassette 110.

The first embodiment of a dialysis machine furthermore has an apparatus for automatic connecting. A connector receiver 112 is provided for this purpose into which the connectors of the dialysate bag 10 are inserted. The connector receiver 112 then moves into the apparatus where a barcode reader is provided which reads the barcodes applied to the connectors. The apparatus can thus check whether the correct bags were inserted. If the correct bags are recognized, the connector receiver 112 moves in completely and so connects the connectors of the bag to the connections 11 of the cassette made as connectors.

In the second embodiment, such an automatic connecting was, in contrast, dispensed with. Hose sections are therefore arranged at the connections 11 of the cassette and have to be manually connected to the corresponding bags via connectors.

2.3 Pump Actuators

The pumping of the liquid through the fluid system takes place in the embodiments by a membrane pump which is formed by the pump chambers 53 and 53' together with the flexible film of the cassette. If the flexible film is in this respect pressed into the pump chamber by a corresponding pump actuator, fluid is pumped out of the pump chamber into the opened regions of the fluid paths of the cassette. Conversely, fluid is sucked out of the fluid paths into the pump chamber by pulling the film out of the pump chamber.

The pump stroke in this respect takes place by movement of a pump actuator into the pump chamber. The pump actuator is moved away from the pump chamber again for the suction stroke. An underpressure arises in this respect due to the airtight pressing of cassette and coupling surface by which the flexible film of the cassette follows the pump actuator and is thus pulled out of the pump chamber again.

To enable a good coupling of the pump actuator to the flexible film of the cassette, a vacuum system can moreover be provided. In this respect, in particular the force with which the flexible film is moved away from the pump chamber at a maximum during a suction stroke can be set via the setting of a corresponding vacuum between the coupling surface and the cassette.

The suction force of the pump can hereby be set very finely. The pump force is in contrast set by the thrust force of the actuator.

The balancing of the fluid flows can in this respect take place by the counting of the suction and pump strokes since the membrane pump has a high precision of the fluid quantity pumped with each stroke.

2.3.1. Hydraulic Drive

The structure of a first embodiment of a pump actuator is shown in FIG. 11. The pump actuator is moved hydraulically in this respect. A membrane 59 is provided for this purpose which is placed at the flexible film of the cassette. The membrane 59 can in this respect be produced e.g. from silicone. A chamber 54 which can be filled with hydraulic fluid is provided behind the membrane 59. By application of an overpressure in the chamber 54, the membrane 59, and with it the flexible film, is pressed into the pump chamber 53 of the cassette. By application of an underpressure to the chamber 54, the membrane 59 is, in contrast, pulled into the chamber 54. Due to the underpressure between the flexible film and the membrane, the flexible film follows this movement so that the volume of the pump chamber 53 increases. The pump process with the pump stroke and the suction stroke is shown schematically in FIG. 12b in this respect.

A hydraulic pump 58 is provided for the operation of the pump hydraulic. It has a cylinder in which a piston can be moved to and fro via a motor 57. The hydraulic fluid is hereby pressed into the chamber 54 or sucked out of it again via a corresponding connection line. A position encoder 56 is provided at the hydraulic pump 58 in this respect and the movement of the piston can be recorded via it. It can hereby be determined how much hydraulic fluid was pressed into the chamber 54 and how much hydraulic fluid was removed from it. Pressure sensors 55 are furthermore provided at the hydraulic system which measure the pressure in the hydraulic system. They on the one hand allow a functional check of the hydraulic system since the data of the pressure sensors can be compared with those of the position encoder 56 and the leak tightness of the hydraulic system can hereby be checked.

In addition, the pressure sensors allow a determination of the pressure in the pump chamber 53 of the cassette. If the hydraulic pump 58 is not moved, a pressure balance is adopted between the chamber 54 and the pump chamber 53. The pressure of the hydraulic fluid thus corresponds to the pressure in the pump chamber 53.

The coupling procedure of the pump actuator to the pump chamber 53 is now shown in FIG. 12a. In this respect, the chamber 54 is first loaded with hydraulic fluid such that the membrane 59 arches outwardly for the preparation of the coupling. The coupling surface and the cassette are thereupon moved toward one another so that the membrane 59 presses the flexible film of the cassette into the pump chamber 53. After the pressing of the coupling surface and of the cassette, the space between the membrane and the flexible film is outwardly closed in an airtight manner so that the flexible film follows the movement of the membrane. This is shown in FIG. 12b.

The pump actuator shown in FIG. 11 is in this respect implemented in the first embodiment of a dialysis machine, as can also be seen from FIG. 7. In this respect, a corresponding pump actuator is respectively provided for each of the two pump chambers 53 and 53'.

2.3.2 Electromechanical Drive

Alternatively, the pump actuator can also be operated in an electric motor manner. A correspondingly shaped ram is provided for this purpose which is pressed toward or away from the flexible film via an electric motor, in particular via a stepped motor, and the pump stroke or suction stroke is thus generated. Such pump actuators 151 and 152 are shown in the embodiment in FIG. 10. A vacuum system is in this respect advantageously provided which ensures that the flexible film also follows the ram in the suction movement.

2.4 Valve Actuators

A valve plunger can be provided as the valve actuator which presses the flexible film of the cassette into a corresponding chamber of the hard part and so closes the fluid passage in this region. The valve actuator can in this respect e.g. be pneumatically actuated. The plunger can in this respect be biased via a spring so that it either opens without pressure or closes without pressure.

Alternatively, the valve actuator can be implemented via a flexible membrane which is moved hydraulically or pneumatically. The flexible membrane is in this respect moved toward the cassette by application of pressure and so presses a corresponding valve region of the flexible film into a fluid passage to close it.

Valve actuators 71, which are coupled to the valve regions V1 to V16 of the cassette, can be recognized on the coupling surface in FIG. 10.

2.5 Sensors

The dialysis machine has sensors via which the machine can be controlled or its proper functioning can be monitored.

On the one hand, in this respect, one or more temperature sensors are provided via which the temperature of the dialysate and/or of the heating elements can be measured. In the first embodiment, the temperature sensors are in this respect arranged at the coupling surface to the cassette and can so measure the temperature of the dialysate flowing through the cassette. In the second embodiment, in contrast, a temperature sensor 88 is provided on the heating plate 68 which measures the temperature of the dialysate present in the bag 67. Temperature sensors can furthermore be provided at the heating element or elements.

One or more pressure sensors can furthermore be provided to determine the pressure in the pump chambers. It can hereby be prevented that dialysate is pumped to the patient at too high a pressure or that the suction pressure becomes too high on the sucking of dialysate from the patient.

In the first embodiment, the pressure measurement takes place in this respect via pressure sensors in the hydraulic system of the pump actuators, as was shown above. In the second embodiment, in contrast, pressure sensors 85' and 86' are provided in the coupling surface which directly measure the pressure in corresponding pressure measurement regions of the cassette. The coupling of these pressure sensors to the cassette is in this respect advantageously ensured by a vacuum system.

2.6 Input/Output Unit

The dialysis machine furthermore includes an input/output unit for communication with an operator. A corresponding display is in this respect provided for the output of information which can e.g. be implemented by light-emitting diodes, LCD displays or a screen. Corresponding input elements are provided for the inputting of commands. Push buttons and switches can e.g. be provided in this respect.

In both embodiments, a touch screen 120 is provided in this respect which allows an interactive menu navigation. Display elements 121 and 122 are furthermore provided which show states of the dialysis machine in compact form.

The first embodiment furthermore has a card reader 125 via which a patient card can be read. Data on the treatment of the respective patient can be stored on the patient card. The treatment procedure for the respective patient can hereby be individually fixed.

The peritoneal dialysis furthermore has an acoustic signal unit via which acoustic signals can be output. In this respect, an acoustic warning signal can in particular be output when an error state is registered. A loudspeaker is in this respect advantageously provided via which the acoustic signals can be generated.

2.7 Controller

The peritoneal dialysis furthermore has a controller by which all components are controlled and monitored. The controller in this respect ensures the automatic procedure of the treatment.

The basic structure of an embodiment of such a controller is now shown in FIG. 13.

The communication with the operator and with external information sources in this respect takes place via an interface computer 150. It communicates with a patient card reader 200, an input and output unit 210 which serves communication with the patient and with a modem 220. Updated software can e.g. be uploaded via the modem 220.

The interface computer 150 is connected via an internal bus to an activity computer 160 and to a protective computer 170. The activity computer 160 and the protective computer 170 generate redundancy of the system. The activity computer 160 in this respect receives signals from the sensors of the system and calculates the control signals for the actuators 180. The protective computer 170 likewise receives signals from the sensors 180 and checks whether the commands output by the activity computer 160 are correct. If the protective computer 170 determines an error, it initiates a corresponding emergency procedure. The protective computer 170 can in particular trigger an alarm signal in this respect. The protective computer 170 can furthermore close the access to the patient. A special valve is arranged at the output of the cassette at the patient side for this purpose and only the protective computer 170 has access to it. This safety valve is in this respect closed in the pressureless state so that it closes automatically on a failure of the pneumatic system.

The protective computer 170 is furthermore connected to the barcode reader 190 and so checks the connection of the correct dialysis bags.

A diagnosis system 230 is furthermore provided via which errors of the system can be determined and remedied.

3. Implementation of the Invention

An embodiment of the two aspects of the present invention which can be used in one of the dialysis systems presented above or in one of the dialysis machines presented above will now be presented in the following. In this respect, the embodiments of the present invention can be combined with individual components or a plurality of components, such as were described above.

In FIG. 14a, a schematic diagram of a device 300 in accordance with the invention with an insulation monitor 350 is shown. The device is in this respect electrically operable via a mains voltage connection 310. In the embodiment, the device in accordance with the invention does not have any ground wire connection. The device includes a live element 320 which is operated via the mains voltage connection 310 without a galvanic coupling. If the live element is therefore switched on, mains voltage is applied to it. In this respect, two mains voltage lines 311 and 312 are provided which supply the live element 320 with mains voltage.

The device in accordance with the invention furthermore has an application part 330 with which a user can come into contact on operation of the device. The application part 330 is in this respect isolated from the live element 320 by a basic insulation 340. A basic protection is hereby provided against the danger of an electric shock. The application part is in this respect electrically conductive in this embodiment so that on a failure of the basic insulation 340, there is a risk of an electric shock for a user who comes into contact with the application part 330.

The device in accordance with the invention is in this respect usually supplied with power via a mains voltage connection of the public mains network (e.g. a 110 V or 230 V mains voltage connection or a corresponding three-phase current connection). One of the two connection lines for the AC current is therefore grounded. If now a fault in the basic insulation occurs, it must be prevented that a user who is in contact with the application part and the ground is hereby exposed to a dangerous current flow.

An insulation monitor 350 is provided for this purpose in accordance with the invention which monitors the quality of the basic insulation 340 of the application part 330 with respect to the live element 320. If a preset limit value is exceeded or fallen below, the insulation monitor 350 in this respect carries out a switching off of the power supply of the live element 320 via the switches 360 and 370. The constant monitoring of the quality of the basic insulation thus makes it possible to provide a safe fault protection even without a ground wire.

In this respect, the insulation monitor 350 is connected via a line 351 to the first voltage feed 311 of the live element 320 and via a second line 352 to the second voltage feed 312 of the live element 320. The connection in this respect takes place via a resistance bridge in the embodiment in shown in FIG. 14a. The insulation monitor is furthermore electrically conductively connected to the application part 330 via a line 353. The insulation monitor can thus constantly monitor the quality of the basic insulation between the application part 340 and the live element 320.

An embodiment of a live element is shown in FIG. 14b. In this respect, this is a ceramic heating element in which a resistance path 321 is arranged as a live element on a ceramic plate 341 which serves as the basic insulation to the heating plate 331 arranged on the ceramic plate 341. The heating plate 331 is advantageously an aluminum plate. The two ends of the resistance path are in this respect connected to the mains voltage lines 311 and 312.

The resistance monitor is now connected via the lines 351 and 352 to the two ends of the resistance path and via the line 353 to the heating plate 331. The heating plate 331 has a corresponding connection 332 for the line 353 for this purpose. The insulation monitor can thus monitor the quality of the insulation 341 between the live resistance path 321 and the heating plate 331. The present invention can naturally, however, also be used with other live elements.

The monitoring of the quality of the insulation can in this respect take place in different manners. In this respect, in FIGS. 15 and 16, two such monitoring principles are shown schematically. In this respect, an electrical device is in each case again shown with a live element 320, an application part 330 and a basic insulation 340. The basic insulation 340 is in this respect made as a double insulation in this embodiment. Furthermore, an insulation monitor 350 is in turn shown which is connected both to the voltage feeds 311 and 312 of the live element 320 and to the application part 330. The circuit arrangement for switching off the mains voltage on the detection of an insulation fault is in this respect not shown in FIGS. 15 and 16, but can be implemented as shown in FIG. 14.

The voltage feed 312 of the mains voltage connection in FIGS. 15 and 16 is marked as a neutral conductor N; the voltage feed 312 is marked as a phase P. Furthermore, a person is shown in FIGS. 15 and 16 respectively whose feet are e.g. in contact with the ground 380. If the person in so doing touches the application part 330 and if the basic insulation 340 is faulty, a dangerously high current can flow from the phase P of the mains connection over the application part and through the person to the ground 380 without the insulation monitor 350. The insulation monitor in accordance with the invention, however, monitors the quality of the basic insulation and switches the power supply of the live part 320 off when it detects a faulty insulation. A dangerous electric shock can thus be prevented.

In this respect, in FIG. 15, a passive insulation monitor is provided which determines the current flow between the voltage feeds 311 and 312 and the application part 330 respectively. If this current flow exceeds a specific limit value, the insulation monitor switches the power supply off.

In FIG. 16, in contrast, an active monitoring of the basic insulation 340 is provided. In this respect, the insulation monitor 350 in each case applies a voltage signal to the voltage feeds 311 and 312 respectively and to the application part 330 and measures the current flow hereby generated. The insulation resistance can hereby be determined.

The device in accordance with the invention is advantageously a device having a housing which can be connected to a mains voltage connection via a mains cable. The device can in this respect in particular advantageously be connected to a socket via a customary two-pole mains plug since no ground wire connection is required. The present invention is used particularly advantageously in medical devices.

In a particularly advantageous embodiment, the device in accordance with the invention is a dialysis machine such as was already shown in more detail above with reference to FIGS. 1 to 13. In this respect, the live element 320 is advantageously a heating element. It is in particular in this respect a ceramic heating element such as has already been described further above. The application part 330 is then advantageously a heating plate such as has likewise already been described further above. This heating plate 330 can in this respect in particular be brought into contact with a heating region of the fluid system to heat the dialyzate.

The present invention enables a dialysis machine to be operated without a ground wire and nevertheless to operate the heating element or elements on the mains without the interposition of an isolating transformer. The insulation monitor in this respect ensures that an operator cannot be endangered by an electric stock even on a failure of the basic insulation between the heating element and the heating plate.

In addition to switching off the power supply for the live element, the insulation monitor can moreover advantageously advise the device controller that the basic insulation is faulty. In this respect, a display can in particular take place which draws the operator's attention to the defectiveness of the basic insulation. Alternatively, however, the power supply of the total device can also be switched off.

Furthermore, the device in accordance with the invention can have an initializing test which checks the function of the insulation monitor when the device is switched on by bridging the basic insulation, e.g. via a switch and a resistor. An additional security with respect to the correct function is hereby ensured.

An embodiment of a heating module in accordance with the second aspect of the present invention is now shown in more detail in FIG. 17. The heating module 400 includes a heating plate 401 on which two heating elements 410 and 420 are applied. Alternatively, in this respect, only a single heating element could naturally also be used, or more than two heating elements.

The heating elements in this respect each have a heating coil which is applied to a ceramic layer. The heating element 410 in this respect has the heating coil 412 which is applied to a ceramic support plate 411.

FIG. 17 in this respect shows the heating module in the upper representation in a view from behind and in a side view in a further representation. In this respect, the layer structure of the heating module with the heating plate 401 and the ceramic support plate 411 for the heating coil can be recognized.

In accordance with the invention, the heating plate 401 on which the heating elements are arranged now also comprises a ceramic material. An additional electrical insulation of the heating module and thus of the medical device is hereby achieved with respect to the heating plates of aluminum used in the prior art.

In the embodiment, the support plate 411 of the heating elements which forms the first ceramic layer and on which the heating coil 412 is arranged comprises aluminum oxide. The heating plate 401 in the embodiment comprises aluminum nitride in the embodiment. Both materials have very good heat-conducting properties with simultaneously very good insulation properties.

The ceramic support plates of the heating elements are in this respect adhered to the heating plate 401 via a thermal adhesive. A silicone adhesive is advantageously used as the thermal adhesive.

In the embodiment, the support plate 411 of the heating elements has a thickness of 1.0 mm, the heating plate 401 has a thickness of 1.5 mm. The layer thickness of the thermal adhesive can amount to between 0.1 mm and 0.5 mm.

The heating elements have connectors 413 for connection to the power supply 440 and connector lines can be connected thereto. Oh the rear side, the connector elements 413 in this respect advantageously project away from the ceramic support plates 411. The heating elements can furthermore each be equipped with a temperature sensor 414. The temperature sensors 414 can likewise include a resistance path, with here connectors 415 being provided for connection to evaluation electronics.

The two heating elements 410 and 420 can be connected to one another via a connection line 430 so that both heating elements are connected in series. Alternatively, however, a connection in parallel would also be conceivable. In this respect, a thermal fuse is advantageously integrated in the connection line 430.

In accordance with the invention, two or more identical heating elements can be used. Two or more heating elements can in particular be arranged next to one another on a common heating plate 401.

The heating plate 401 in this respect advantageously projects in its marginal regions beyond the support plates 411 of the heating elements. Further advantageously, the respective ceramic plates 411 and 401 do not have any apertures.

The heating plate 401 can additionally be adhered to a frame to stabilize the total heating module. Provision can furthermore be made that the total heating module is vulcanized into the housing of the medical device, in particular into the drawer or the machine block.

The heating module in accordance with the invention can be used in the same manner as the heating already presented above in section 2.1. The heating module is, as described there, in particular used for heating the dialysate. The heating plate 401 can in this respect advantageously be directly coupled to the fluid paths of the dialysis machine, for example to a heating region of a cassette or to a heating bag.

A heating module in accordance with the second aspect of the present invention can naturally also be combined with an insulation monitor such as was shown in more detail further above with respect to FIGS. 14 and 16. The heating module in accordance with the invention can in particular be used instead of the heating module shown in FIG. 14b. The connection of the line 353 then, however, naturally does not take place at the ceramic heating plate 401, which is not conductive, but rather at a conductive housing element. A further increased security can hereby be achieved.

In accordance with the invention, however, the second aspect of the present invention also allows on its own a ground wire to be dispensed with and nevertheless to operate the heating module at the mains without the interposition of an isolating transformer. The second insulation layer formed by the ceramic heating plate 401 in this respect ensures that an operator cannot be at risk from an electric shock even on a failure of the base insulation between the heating coil and the heating plate.

The present invention thus enables in both aspects independently of one another a fault protection for the basic insulation which ensures that there is no danger for the user even with a defective basic insulation.

The invention claimed is:

1. A device operable electrically via a mains voltage connection, the mains voltage connection providing a connection to a mains voltage power supply for downloading electrical power from the mains voltage power supply to operate the device, the device having a live element that directly receives the electrical power from the mains voltage power supply via the mains voltage connection to operate the live element, and an application part, wherein the application part is insulated by a basic insulation with respect to the live element,
characterized in that an insulation monitor is provided which monitor the quality of the basic insulation of the application part with respect to the live element, and wherein said device is at least one of a heating element or a medical device.

2. A device in accordance with claim 1, wherein the device is a medical device.

3. A device in accordance with claim 2, wherein the device is a dialysis machine.

4. A device in accordance with claim 1, wherein the insulation monitor determines a current flow and/or a resistance between the live element and the application part by active measurement.

5. A device in accordance with claim 4, wherein the insulation monitor determines the current flow and/or the resistance between the application part and a first voltage feed of the live element and also between the application part and a second voltage feed of the live element.

6. A device in accordance with claim 1, wherein the live element is operated without a galvanic isolation at the mains voltage.

7. A device in accordance with claim 1, wherein the insulation monitor switches the power supply of the live element off when it recognizes a defective basic insulation.

8. A device in accordance with claim 1, wherein the device controller has a function for testing the insulation monitor.

9. A device in accordance with claim 8, wherein the function for testing the proper function of the insulation monitor comprises an initializing test.

10. A device in accordance with claim 1, wherein the live element is a heating element.

11. A device in accordance with claim 1, wherein the application part is a housing element.

12. A method for operating an electrical device as claimed in claim 1 via a mains voltage connection, wherein the device has a live element and an application part, wherein the application part is insulated from the live element by a basic insulation, characterized in that the quality of the basic insulation of the application part is monitored with respect to the live element.

13. A device in accordance with claim 1, wherein the device does not have a ground wire connection.

14. A device in accordance with claim 1, wherein the application part is a heating plate.

15. A dialysis machine operable electrically via a mains voltage connection, the mains voltage connection providing a connection to a mains voltage power supply for downloading electrical power from the mains voltage power supply to operate the dialysis machine, the dialysis machine having a heating element that directly receives the electrical power from the mains voltage power supply via the mains voltage connection to operate the heating element, and a heating plate, wherein the heating plate is insulated by a basic insulation with respect to the heating element, characterized in that an insulation monitor is provided which monitors the quality of the basic insulation of the heating plate with respect to the heating element.

16. A medical device free of any ground wire connection and comprising,
a mains voltage input connected to provide mains voltage directly to a live element of the medical device, said live element being ungrounded and free of any galvanic isolation with respect to said mains voltage,
said medical device further comprising an ungrounded application part contactable by a user of the medical device, and an ungrounded basic insulation for electrically isolating the application part from the live element and thus preventing electric shock to the user, and
an insulation monitor to monitor the quality of the basic insulation by determining a current flow and/or resistance between the live element and application part and to switch off the mains voltage being supplied to the live element when the insulation is recognized as defective.

17. The medical device of claim 16, wherein the medical device is a dialysis machine, the live element is a heating element, and the application part is a heating plate.

* * * * *